(12) United States Patent
Shafer et al.

(10) Patent No.: US 7,269,457 B2
(45) Date of Patent: Sep. 11, 2007

(54) METHOD AND SYSTEM FOR VAGAL NERVE STIMULATION WITH MULTI-SITE CARDIAC PACING

(75) Inventors: Lisa L. Shafer, Stillwater, MN (US); Steve R. LaPorte, Arden Hills, MN (US); James R. Keogh, Maplewood, MN (US); Michael R. S. Hill, Minneapolis, MN (US); Matthew D. Bonner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 544 days.

(21) Appl. No.: 10/737,493

(22) Filed: Dec. 16, 2003

(65) Prior Publication Data

US 2004/0172075 A1 Sep. 2, 2004

Related U.S. Application Data

(63) Continuation-in-part of application No. 10/421,459, filed on Apr. 23, 2003, now Pat. No. 6,904,318, and a continuation-in-part of application No. 10/207,725, filed on Jul. 29, 2002, now Pat. No. 6,718,208, which is a continuation of application No. 09/669,961, filed on Sep. 26, 2000, now abandoned, which is a continuation-in-part of application No. 09/670,441, filed on Sep. 26, 2000, now Pat. No. 6,449,507, which is a continuation-in-part of application No. 09/433,323, filed on Nov. 3, 1999, now Pat. No. 6,266,564, which is a continuation of application No. 09/070,506, filed on Apr. 30, 1998, now Pat. No. 6,006,134, which is a continuation-in-part of application No. 08/640,013, filed on Apr. 30, 1996, now abandoned.

(51) Int. Cl.
*A61N 1/362* (2006.01)

(52) U.S. Cl. .................. 607/9; 607/2; 607/10; 607/17
(58) Field of Classification Search ..................... None
See application file for complete search history.

(56) References Cited

U.S. PATENT DOCUMENTS 3,614,995 A 10/1971 Probert et al.

(Continued)

FOREIGN PATENT DOCUMENTS

AU 9890156 3/1999

(Continued)

OTHER PUBLICATIONS

U.S. Appl. No. 09/980,421.

(Continued)

*Primary Examiner*—Carl Layno
(74) *Attorney, Agent, or Firm*—Ingrassia Fisher & Lorenz, P.C.

(57) ABSTRACT

A method of performing a medical procedure is provided. The medical procedure includes stimulation of a patient's heart while stimulating a nerve of the patient in order to modulate the patient's inflammatory process. More particularly, the medical procedure includes pacing the ventricles of the patient's heart while stimulating the vagal nerve of the patient. Systems and devices for performing the medical procedure are also provided.

86 Claims, 9 Drawing Sheets

U.S. PATENT DOCUMENTS

| | | |
|---|---|---|
| 3,804,098 A | 4/1974 | Friedman |
| 3,937,226 A | 2/1976 | Funke ................... 128/419 D |
| 4,088,138 A | 5/1978 | Diack et al. |
| 4,088,140 A | 5/1978 | Rockland et al. ..... 128/419 PG |
| 4,161,952 A | 7/1979 | Kinney et al. |
| 4,176,660 A | 12/1979 | Mylrea et al. |
| 4,198,963 A | 4/1980 | Barkalow et al. |
| 4,303,075 A | 12/1981 | Heilman et al. ....... 128/419 PG |
| 4,304,239 A | 12/1981 | Perlin ........................ 128/642 |
| 4,321,929 A | 3/1982 | Lemelson et al. |
| 4,332,259 A | 6/1982 | McCorkle, Jr. ............. 128/786 |
| 4,351,330 A | 9/1982 | Scarberry |
| 4,354,497 A | 10/1982 | Kahn .................... 128/419 D |
| 4,458,677 A | 7/1984 | McCorkle, Jr. ............. 128/786 |
| 4,548,203 A | 10/1985 | Tacker, Jr. et al. ...... 128/419 D |
| 4,574,807 A | 3/1986 | Hewson et al. |
| 4,603,705 A | 8/1986 | Speicher et al. |
| 4,640,298 A | 2/1987 | Pless et al. ................. 128/784 |
| 4,671,295 A | 6/1987 | Abrams et al. |
| 4,715,367 A | 12/1987 | Crossley |
| 4,722,347 A | 2/1988 | Abrams et al. |
| 4,753,244 A | 6/1988 | Landymore et al. |
| 4,919,147 A | 4/1990 | Reinhardt et al. |
| 4,928,688 A | 5/1990 | Mower ................. 128/419 PG |
| 4,929,688 A | 5/1990 | Allen et al. |
| 4,931,464 A | 6/1990 | Grover et al. |
| 4,952,586 A | 8/1990 | Morris et al. |
| 4,960,133 A | 10/1990 | Hewson ....................... 128/784 |
| 5,003,991 A | 4/1991 | Takayama et al. |
| 5,007,893 A | 4/1991 | Row |
| 5,014,698 A | 5/1991 | Cohen .................... 128/419 D |
| 5,024,228 A | 6/1991 | Goldstone et al. |
| 5,025,807 A | 6/1991 | Zabara |
| 5,036,848 A | 8/1991 | Hewson |
| 5,044,367 A | 9/1991 | Endres et al. ........... 128/419 R |
| 5,050,600 A | 9/1991 | Parks |
| 5,052,390 A | 10/1991 | Hewson .................. 128/419 D |
| 5,056,519 A | 10/1991 | Vince ..................... 128/419 G |
| 5,056,532 A | 10/1991 | Hull et al. ................... 128/785 |
| 5,117,822 A | 6/1992 | Laghi |
| 5,117,828 A | 6/1992 | Metzger et al. |
| 5,125,406 A | 6/1992 | Goldstone et al. |
| 5,127,407 A | 7/1992 | Tan |
| 5,129,392 A | 7/1992 | Bardy et al. ............ 128/419 D |
| 5,154,172 A | 10/1992 | Terry, Jr. et al. |
| 5,156,149 A | 10/1992 | Hudrlik |
| 5,156,151 A | 10/1992 | Imran |
| 5,174,289 A | 12/1992 | Cohen .................. 128/419 PG |
| 5,178,149 A | 1/1993 | Imburgia et al. |
| 5,179,950 A | 1/1993 | Stanislaw |
| 5,179,952 A | 1/1993 | Buinevicius et al. |
| 5,186,170 A | 2/1993 | Varrichio et al. |
| 5,188,104 A | 2/1993 | Wernicke et al. |
| 5,199,428 A | 4/1993 | Obel et al. .............. 128/419 C |
| 5,203,326 A | 4/1993 | Collins ................. 128/419 PG |
| 5,205,285 A | 4/1993 | Baker, Jr. |
| 5,215,086 A | 6/1993 | Terry, Jr. et al. |
| 5,231,988 A | 8/1993 | Wernicke et al. |
| 5,235,980 A | 8/1993 | Varrichio et al. |
| 5,243,980 A | 9/1993 | Mehra ........................... 607/6 |
| 5,263,480 A | 11/1993 | Wernicke et al. |
| 5,265,603 A | 11/1993 | Hudrlik |
| 5,265,623 A | 11/1993 | Kroll et al. |
| 5,267,560 A | 12/1993 | Cohen ......................... 607/25 |
| 5,269,303 A | 12/1993 | Wernicke et al. |
| 5,282,468 A | 2/1994 | Klepinski |
| 5,284,146 A | 2/1994 | Czar et al. |
| 5,292,338 A | 3/1994 | Bardy ............................ 607/5 |
| 5,299,569 A | 4/1994 | Wernicke et al. |
| 5,304,120 A | 4/1994 | Crandell et al. |
| 5,304,206 A | 4/1994 | Baker, Jr. et al. |
| 5,304,220 A | 4/1994 | Maginot |
| 5,306,293 A | 4/1994 | Zacouto |
| 5,330,507 A | 7/1994 | Schwartz ..................... 607/14 |
| 5,330,515 A | 7/1994 | Rutecki et al. ............... 607/46 |
| 5,334,221 A | 8/1994 | Bardy ......................... 607/14 |
| 5,335,657 A | 8/1994 | Terry, Jr. et al. |
| 5,354,318 A | 10/1994 | Taepke ........................ 607/22 |
| 5,356,425 A | 10/1994 | Bardy et al. ................. 607/14 |
| 5,365,926 A | 11/1994 | Desai |
| 5,379,765 A | 1/1995 | Kajiwara et al. |
| 5,403,356 A | 4/1995 | Hill et al. ..................... 607/14 |
| 5,411,529 A | 5/1995 | Hudrlik |
| 5,417,713 A | 5/1995 | Cohen |
| 5,456,254 A | 10/1995 | Pietroski et al. |
| 5,458,625 A | 10/1995 | Kendall |
| 5,476,485 A | 12/1995 | Weinberg et al. |
| 5,501,702 A | 3/1996 | Plicchi et al. ................. 607/20 |
| 5,501,703 A | 3/1996 | Holsheimer et al. .......... 407/46 |
| 5,507,784 A | 4/1996 | Hill et al. ..................... 607/14 |
| 5,514,161 A | 5/1996 | Limousin ....................... 607/9 |
| 5,531,776 A | 7/1996 | Ward et al. |
| 5,540,730 A | 7/1996 | Terry, Jr. et al. .............. 607/40 |
| 5,540,732 A | 7/1996 | Testerman ................... 607/42 |
| 5,549,655 A | 8/1996 | Erickson ...................... 607/42 |
| 5,571,150 A | 11/1996 | Wernicke et al. ............. 607/72 |
| 5,578,061 A | 11/1996 | Stroetmann et al. ........... 607/4 |
| 5,584,867 A | 12/1996 | Limousin et al. ............... 607/9 |
| 5,611,350 A | 3/1997 | John ........................ 128/731 |
| 5,620,468 A | 4/1997 | Mongeon et al. ............... 607/5 |
| 5,651,378 A | 7/1997 | Matheny et al. ............ 128/898 |
| 5,656,420 A | 8/1997 | Chien |
| 5,662,689 A | 9/1997 | Elsberry et al. |
| 5,668,117 A | 9/1997 | Shapiro |
| 5,674,259 A | 10/1997 | Gray ............................ 607/20 |
| 5,690,681 A | 11/1997 | Geddes et al. ................. 607/2 |
| 5,700,282 A | 12/1997 | Zabara ......................... 607/9 |
| 5,707,400 A | 1/1998 | Terry, Jr. et al. |
| 5,713,924 A | 2/1998 | Min et al. |
| 5,713,929 A | 2/1998 | Hess et al. |
| 5,720,768 A | 2/1998 | Verboven-Nelissen ......... 607/9 |
| 5,755,682 A | 5/1998 | Knudson et al. |
| 5,782,874 A | 7/1998 | Loos |
| 5,791,187 A | 8/1998 | Chang |
| 5,792,187 A | 8/1998 | Adams ........................... 607/5 |
| 5,792,203 A | 8/1998 | Schroeppel .................. 607/30 |
| 5,797,970 A | 8/1998 | Pouvreau ....................... 607/9 |
| 5,799,661 A | 9/1998 | Boyd et al. |
| 5,824,021 A | 10/1998 | Rise |
| 5,836,994 A | 11/1998 | Bourgeois .................... 607/40 |
| 5,840,076 A | 11/1998 | Swanson et al. |
| 5,846,263 A | 12/1998 | Peterson et al. |
| 5,846,264 A | 12/1998 | Andersson et al. |
| 5,874,420 A | 2/1999 | Pelleg |
| 5,889,033 A | 3/1999 | Kaminski |
| 5,893,881 A | 4/1999 | Elsberry et al. |
| 5,893,882 A | 4/1999 | Peterson et al. |
| 5,902,324 A | 5/1999 | Thompson et al. ............. 607/9 |
| 5,913,876 A | 6/1999 | Taylor et al. ................... 607/2 |
| 5,916,239 A | 6/1999 | Geddes et al. ................. 607/14 |
| 5,928,272 A | 7/1999 | Adkins et al. ................. 607/45 |
| 5,964,789 A | 10/1999 | Karsdon ...................... 607/39 |
| 5,971,911 A | 10/1999 | Wilk |
| 5,977,408 A | 11/1999 | Levin et al. ................. 562/622 |
| 5,995,872 A | 11/1999 | Bourgeois |
| 5,998,386 A | 12/1999 | Feldman ...................... 514/46 |
| 6,006,134 A | 12/1999 | Hill et al. ...................... 607/9 |
| 6,007,559 A | 12/1999 | Arkans |
| 6,014,588 A | 1/2000 | Fitz |
| 6,042,538 A | 3/2000 | Puskas |
| 6,043,273 A | 3/2000 | Duhaylongsod ............. 514/478 |
| 6,060,454 A | 5/2000 | Duhaylongsod ............. 514/26 |
| 6,073,048 A | 6/2000 | Kieval et al. ................. 607/17 |
| 6,087,394 A | 7/2000 | Duhaylongsod ............. 514/478 |

| | | |
|---|---|---|
| 6,091,988 A | 7/2000 | Warman et al. |
| 6,101,412 A | 8/2000 | Duhaylongsod ............... 607/2 |
| 6,103,722 A | 8/2000 | Schultz et al. |
| 6,127,410 A | 10/2000 | Duhaylongsod ............ 514/478 |
| 6,141,589 A | 10/2000 | Duhaylongsod ............. 607/10 |
| 6,141,590 A | 10/2000 | Renirie et al. |
| 6,185,459 B1 | 2/2001 | Mehra et al. |
| 6,221,851 B1 | 4/2001 | Feldman ..................... 514/46 |
| 6,234,985 B1 | 5/2001 | Lurie et al. |
| 6,253,108 B1 | 6/2001 | Rosborough et al. |
| 6,266,564 B1 | 7/2001 | Hill et al. |
| 6,272,380 B1 | 8/2001 | Warman et al. |
| 6,299,564 B1 | 10/2001 | Gessler et al. |
| 6,303,293 B1 | 10/2001 | Patterson et al. |
| 6,304,777 B1 | 10/2001 | Ben-Haim et al. |
| 6,381,499 B1 | 4/2002 | Taylor |
| 6,414,018 B1 | 7/2002 | Duhaylongsod |
| 6,429,217 B1 | 8/2002 | Puskas |
| 6,442,429 B1 | 8/2002 | Hill et al. |
| 6,449,507 B1 | 9/2002 | Hill et al. |
| 6,473,644 B1 | 10/2002 | Terry, Jr. et al. ................ 607/2 |
| 6,479,523 B1 | 11/2002 | Puskas |
| 6,487,446 B1 | 11/2002 | Hill et al. |
| 6,532,388 B1 | 3/2003 | Hill et al. |
| 6,537,540 B1 | 3/2003 | Burstein et al. ........... 424/93.2 |
| 6,542,774 B2 | 4/2003 | Hill et al. |
| 6,554,781 B1 | 4/2003 | Carter et al. |
| 6,572,895 B2 | 6/2003 | Smith et al. ................ 424/529 |
| 6,587,719 B1 | 7/2003 | Barrett et al. |
| 6,589,954 B1 | 7/2003 | Mavunkel et al. .......... 514/253 |
| 6,609,025 B2 | 8/2003 | Barrett et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,690,973 B2 | 2/2004 | Hill et al. |
| 6,711,436 B1 | 3/2004 | Duhaylongsod |
| 6,718,208 B2 | 4/2004 | Hill et al. |
| 6,721,603 B2 | 4/2004 | Zabara et al. |
| 6,735,471 B2 | 5/2004 | Hill et al. |
| 6,738,667 B2 | 5/2004 | Deno et al. |
| 6,778,854 B2 | 8/2004 | Puskas |
| RE38,654 E | 11/2004 | Hill et al. |
| RE38,705 E | 2/2005 | Hill et al. |
| 6,904,318 B2 | 6/2005 | Hill et al. |
| 6,912,419 B2 | 6/2005 | Hill et al. |
| 2001/0049543 A1 | 12/2001 | Kroll .......................... 607/28 |
| 2002/0072782 A1 | 6/2002 | Osorio et al. |
| 2002/0198570 A1 | 12/2002 | Puskas |
| 2002/0198571 A1 | 12/2002 | Puskas |
| 2003/0045909 A1 | 3/2003 | Gross et al. |
| 2003/0074039 A1 | 4/2003 | Puskas |
| 2003/0216775 A1 | 11/2003 | Hill et al. |
| 2003/0216790 A1 | 11/2003 | Hill et al. |
| 2004/0024422 A1 | 2/2004 | Hill et al. |
| 2004/0059383 A1 | 3/2004 | Puskas |
| 2004/0111118 A1 | 6/2004 | Hill et al. |
| 2004/0162584 A1 | 8/2004 | Hill et al. |
| 2004/0172075 A1 | 9/2004 | Shafer et al. |
| 2004/0186517 A1 | 9/2004 | Hill et al. |
| 2004/0186531 A1 | 9/2004 | Jahns et al. |
| 2004/0199209 A1 | 10/2004 | Hill et al. |
| 2005/0096707 A1 | 5/2005 | Hill et al. |
| 2005/0143412 A1 | 6/2005 | Puskas |

FOREIGN PATENT DOCUMENTS

| | | |
|---|---|---|
| AU | 779255 | 6/2000 |
| CA | 2310183 | 5/1996 |
| CA | 2376903 | 6/2000 |
| DE | 28 11 325 | 9/1979 |
| EP | 0440111 | 8/1991 |
| EP | 0 589 252 | 9/1993 |
| EP | 1005337 | 6/2000 |
| EP | 1051168 | 11/2000 |
| EP | 1181947 | 2/2002 |
| JP | 2000-507363 | 8/1998 |
| JP | 2001-505980 | 6/2000 |
| MX | 2043 | 8/1998 |
| WO | WO92/11064 | 7/1992 |
| WO | WP 97/40885 | 11/1997 |
| WO | WO99/00057 | 1/1999 |
| WO | WO99/07354 | 2/1999 |
| WO | WO99/09971 | 3/1999 |
| WO | WO99/09973 | 3/1999 |
| WO | WO99/63926 | 12/1999 |
| WO | WO 00/01306 | 1/2000 |
| WO | WO 00/09206 | 2/2000 |
| WO | WO01/00273 | 6/2000 |
| WO | WO 01/89526 | 11/2001 |
| WO | WO 02/26320 | 4/2002 |

OTHER PUBLICATIONS

Agnew, William F., et al., Considerations for Safety with Chronically Implanted Nerve Electrodes, Epilepsia, 31(Supp. 2), 1990, pp. S27-S32, Raven Press, Ltd., New York.

Bell, et al., "Inotropic Responses of the Left Ventricle to Changes in Heart Rate in Anesthetized Rabbits," Can. J. Physiol. Pharmacol., 65:179-184.

Bennetti, F.J., Direct Coronary Surgery with Saphenous Vein Bypass Without Either Cardiopulmonary Bypass or Cardiac Arrest, J. Cardiovasc. Surg., 26:217-222.

Benetti, et al., "Use of Thoracoscopy and a Minimal Thoracotomy, in Mammary-Coronary Bypass to Left Anterior Descending Artery, Without Extracorporeal Circulation," J. Cardiovasc. Surg., 36:159-161.

Bilgutay, A., et al., "Vagal Tuning: A New Concept in the Treatment of Supraventricular Arrhythmias, Angina pectoris, and Heart failure," Jour. of Thorac. & Cardio. Surg., 1968, pp. 71-82.

Bluemel, K.M., et al., "Parasympathetic Postganglionic Pathways to the Sinoatrial Node," Am. Phys. Soc., 1990, pp. H1504-H1508.

Braunwald, E., et al., "Cartoid Sinus Nerve Stimulation in the Treatment of Angina Pectoris and Supraventricular Tachycardia," Western Jour. of Medicine, 1970, No. 112, vol. 3, pp. 41-50.

Declaration/Clarification of John D. Puskas, MD., dated Oct. 11, 2005, pp. 1-7.

DiMarco, J. P., M.D., et al., "Adenosine: Electrophysiologic Effects and Therapeutic Use for Terminating Paroxysmal Supraventricular Tachycardia," Therapy and Prevention Arrhythmia, Circulation 68, No. 6, 1983, pp. 1254-1263.

Dipiro, J., et al., "Pharmacotherapy: A Pathophysiologic Approach," p. 153-157, 1989.

Fanning, et al., "Reoperative Coronary Artery Bypass Grafting Without Cardiopulmonary Bypass," Ann. Thorac. Surg., 55:486-489.

Freilich, A., M.D., et al., "Adenosine and its Cardiovascular Effects," American Heart Journal, vol. 123, No. 5, May 1992, pp. 1324-1328.

Gorman, Christine, et al., "How New Heart-Scanning Technology Could Save Your Life," *Time*, Sep. 5, 2005, pp. 61 and 67.

Hageman, G.R., et al., "Direct and Reflex Cardiac Bradydysrhythmias from a Small Vagal Nerve Stimulations," Am. Heart J. Mar. 1975; 89: 338-48 (Abstract only).

Hammond, Edward J., et al., "Vagus Nerve Stimulation in Humans: Neurophysiological Studies and Electrophysiological Monitoring," Epilepsia, 31 Suppl. 2), 1990, pp. S51-S59, Raven Press, Ltd., New York.

Klassen, et al., "Coronary Venous Pressure and Flow: Effects of Vagal Stimulation, Aortic Occlusion, and Vasodilators," Can. J. Physiol. Pharmacol., 1984, 62:531-538.

Levy, M. et al., "Autonomic Control of Cardiac Pacemaker Activity and Atrioventricular Transmission," Journal of Applied Physiology, vol. 27, No. 4, Oct. 1969.

Lockard, Joan S., et al., "Feasibility and Safety of Vagal Stimulation in Monkey Model," Epilepsia, 31 (Supp. 2), 1990, pp. S20-S26, Raven Press, Ltd., New York.

Mohiuddin, S. M., M.D., et al., "Safety of Different Dosages of Intravenous Adenosine Used in Conjunction with Diagnostic Myocardial Imaging Techniques," Pharmacotherapy, 1993, 13(5), pp. 476-480.

Nobrega, et al., "Resting and Reflex Heart Rate Responses During Cholinergic Stimulation With Pyridostigmine in Humans," Brazilian J. Med. Biol. Res, vol. 29, No. 11, pp. 1461-1465, 1996 (Abstract Only).

Noonan, David, "And the Beat Goes On," Newsweek, Jul. 11, 2005, pp. 56-57.

Okazawa, M., et al., "Effect of Vagal Stimulations and Parenteral Acetylcholine on Canine Trachealis Muscle Shortening," J. Appl. Physiol., vol. 72, No. 6, pp. 2463-2468, 1992 (Abstract Only).

Penry, J. Kiffin, et al., "Prevention of Intractable Partial Seizures by Intermittent Vagal Stimulation in Humans: Preliminary Results," Epilepsia, 31 (Suppl. 2), 1990, pp. S40-S43, Raven Press, Ltd., New York.

Pfister, et al., "Coronary Artery Bypass Without Cardiopulmonary Bypass," Ann. Thorac. Surg., 54:1085-92.

Randall, Walter C., PhD., "Parasympathetic Control of the Heart," Chapter 4, Nervous Control of Cardiovascular Function, 1984, pp. 68-94.

Randall, Walter C., Ph.D. et al., "Functional Anatomy of the Cardiac Efferent Innervation," Neurocardiology, 1988, pp. 3-24.

Reid, Steven A., "Surgical Technique for Implantation of the Neurocybernetic Prothesis," Epilepsia, 1990, 31 (supp. 2): S38-S39.

Rutecki, Paul, "Anatomical, Physiological, and Theoretical Basis for the Antiepileptic Effect of Vagus Nerve Stimulation," Epilepsia, 31(Suppl. 2), 1990, pp. S2-S6, Raven Press, Ltd., New York.

Subramanian, V.A., "Clinical Experience with Minimally Invasive Reoperative Coronary Bypass Surgery," Eur. J Cardio-Thorac Surg, 1996, 10:1058-1062.

Taylor, P., "Anticholinesterase Agents" Goodman and Gilman's, The Pharmacological Basis of Therapeutics, 6th Ed. MacMillan Publishing Co., Inc., New York, pp. 93-94 and 104-108, 1980.

Terry, Reese, et al., "An Implantable Neurocybernetic Prosthesis System," Epilepsia, 31 (Suppl. 2), 1990, pp. S33-S37, Raven Press, Ltd. New York.

Thompson, et al., "Bradycardia Induced by Intravascular Versus Direct Stimulation of the Vagus Nerve," Ann. Thorac. Surg., 1998; 65: 637-42.

Urthaler, James F., "Experimental Studies on the Pathogenesis of Asystole After Verapamil in the Dog," Am. J. Cardiol., vol. 44, No. 4, ppl 651-656, 1979 (Abstract Only).

Uthman, Basim M., et al., "Efficacy and Safety of Vagus Nerve Stimulation in Patients with Complex Partial Seizures," Epilepsia, 31(Suppl. 2), 1990, p. S44-S50, Raven Press, Ltd., New York.

Westaby, S., "Coronary Surgery Without Cardiopulmonary Bypass," British Heart Journal, 73:203-205.

Wilder, B.J., et al., "Vagus Nerve Stimulation for the Control of Epilepsy," Proceedings of a Symposium held in conjunction with the American Epilepsy Society Annual Meeting, Boston, MA, Dec. 2, 1989, vol. 31, Supplement 2, 1990.

Woodbury, Dixon M., et al., "Effects of Vagal Stimulation on Experimentally Induced Seizures in Rats," Epilepsia, 31(Suppl. 2), 1990, pp. S7-S19, Raven Press, Ltd., New York.

Coronary Artery Surgery With Induced Temporary Asystole And Intermittent Ventricular Pacing: An Experimental Study / R. Khanna and H.C. Cullen / Cardiovascular Surgery/ Apr. 1996 vol. 4 No. 2 pp. 231-236.

Editorial / Adrian R.M. Upton / PACE, October, Part II 1992 vol. 15 pp. 1543-1544.

Neural Effects On Sinus Rate and Atrioventricular Conduction Produced by Electrical Stimulation from a Transvenous Electrode Catheter in the Canine Right Pulmonary Artery / Terry B. Cooper, Gilbert R. Hageman, Thomas N. James, and Albert L. Waldo / Circulation Research vol. 46, No. 1, Jan. 1980.

Selective Stimulation of Parasympathetic Nerve Fibers to the Human Sinoatrial Node / Mark D. Carlson, MD, MA; Alexander S. Geha, MD, MS; Jack Hsu, MD; Paul J. Martin, PhD; Matthew N. Levy, MD; Gretta Jacobs, MD; and Albert I. Waldo, MD / Circulation—vol. 85, No. 4 pp. 1311-1317.

Controlled Intermittent Asysteole: Pharmacologic Potentiation of Vagal-Induced Asystole / Bradley L. Burkin, MD; John D. Puskas, MD; Jakob Vinten-Johansen, PhD; Steven T. Shearer, BS; and Robert A. Guyton, MD / The Society of Thoracic Surgeons—1998.

Controlled Ventricular Asystole With Surgeons—Actuated Pacing For Off-Pump Coronary Artery Bypass Grafting: A Proposed Surgical Method / Francis G. Duhaylongsod and William R. Burfeind, Jr. / IBMCS Abstract —Jun. 25, 1998.

Age-related Changes of Cardiac Control Function in Man: With special reference to heart rate control at rest and during exercise. / Iwao Sato, MD; Yasuhiro Hasegawa, MD; Norikazu Takahashi, MD; Yukio Hirata, MD; Katsuro Shimomura, MD; and Ken Hotta, PhD. / Journal of Gerontology, 1981, vol. 36, No. 5, pp. 564-572.

Cardiac Muscarinic Receptors Decrease with Age / Otto-Erich Brodde; Ulrich Konschak; Karin Becker, Florian Ruter; Ulrike Potter; Jens Jakubetz; Joachim Radke; and Hans-Reinhard Zerkowski / J. Clin. Invest. vol. 101, No. 2. Jan. 1998, 471-478.

Age-Dependent Changes in Cardiac Muscarinic Receptor Function in Healthy Volunteers / Ulrike Pller, MD; Gesine Nedelka, MD; Joachim Radke, MD; Klaus Poinicke, Ph.D.; and Otto-Erich Brodde, Ph.D. / JACC vol. 29. No. 1 Jan. 1997: 187-93

Age-Related Changes of Cardiac Parasympathetic Modulation After Vasovagal Syncope / Alfonso Lagi, MD; Simone Cencetti, MD; Lamberto Fattorini, MD; and Carlo Tamburini, MD / The American Journal of Cardiology vol. 83 Mar. 15, 1999.

Desensitization of the Cholinergic receptor at the sinoatrial cell of the kitten / Jose Jalife; Allan J. Hamilton, and Gordon K. Moe / 1980 the American Physiological Society.

Sensitivity differences of SA and AV node to vagal stimulation: attenuation of vagal effects at SA node / Jerod M. Loeb; Daniel P. Dalton; and John M. Moran / 1981 the American Physiological Society.

Vagal Nerve Monitoring: A Comparison of Techniques in a Canine Model / Mark A. Severtson; John P. Leonette; and Denise Jarocki / The American Journal of Otology 18:398-400 1997.

The NIM-2 nerve integrity monitor in thyroid and parathyroid surgery / J. Barwell; J. Lytle; R. Page; and D. Wilkins / British Journal of Surgery 1997, 84, 854.

A New Method For Intraoperative Recurrent Laryngeal Nerve Monitoring / Richard W. Maloney, MD; Benjamin W. Murcek, DO; Kirk W. Steehler, DO; Dennis Sibly; Richard E. Maloney / ENT Journal Jan. 1994.

Revision and Removal of Stimulating Electrodes Following Long-Term Therapy with the Vagus Nerve Stimulator / Jose Espinosa, MD; Mary T. Aiello, MA; and Dean K. Naritoku, MD / 1999 by Elsevier Science Inc. / Surg Neurol 1999:51:659-64.

Epilepsy, Vagal Nerve Stimulation by the NCP System, All-Cause Mortality, and Sudden, Unespected, Unexplained Death / J.F. Annegers; Sharon P. Coan; W.A. Hauser; and J. Leestma / Epilepsia, vol. 41. No. 5. 2000.

Fade of cardiac responses during tonic vagal stimulation / Paul Martin, Matthew N. Levy, and Yasuo Matsuda / 1982 the American Physiological Society.

Experiences in Minimally Invasive Cardiac Surgery—Techniques of Stabilization / Robert G. Matheny, MD / presented by the Minneapolis Heart Institute Foundation Jun. 19-21, 1997.

Vagus Nerve Stimulation as a Method to Temporarily Slow or Arrest the Heart / Robert G. Matheny, MD; and Carl J. Shaar, PhD / 1997 by The Society of Thoracic Surgeons.

Vagus Nerve Stimulation for Treatment of Partial Seizures: 1. A Controlled Study of Effect on Seizures / E. Ben-Menachem, R. Manon-Espaillat; R. Ristanovic; B.J. Wilder; H. Stefan; W. Mirza; W.B. Tarver; J.F. Wernicke; and First International Vagus Nerve Stimulation Study Group / Epilepsia, 35(3):616-626, 1994.

Vagus Nerve Stimulation for Treatment of Partial Seizures: 2. Safety, Side Effects, and Tolerability / R.E. Ramsay; B.M. Uthman; L.E. Augustinsson; A.R.M. Upton; D. Naritoku; J. Willis; T. Treig; G. Barolat; J.F. Wernicke; and First International Nerve Stimulation Study Group / Epilepsia. 35(3) 627-636, 1994.

Vagus Nerve Stimulation for Treatment of Partial Seizures: 3. Long-Term Follow-Up On First 67 Patients Exiting a Controlled Study / R. George; M. Salinsky; R. Kuzniedky; W. Rosenfeld; D. Bergen; W. B. Tarver; J.F. Wernicke; and First International Nerve Stimulation Study Group / Epilepsia. 35(3):637-643, 1994.

Vagus Nerve Stimulation for the Control of Epilepsy / Epilepsia Jorunal of the International League Against Epilepsy / Proceedings of a Symposium held I conjunction with the American Epilepsy Society Annual Meeting Boston, MA Dec. 2, 1989.

Inflammatory Mediators and the Failing Heart: A Translational Approach / Abhinav Diwan, Tony Tran, Arunima Misra and Douglas L. Mann / Curr Mol Med. 2003: 3:161-82.

The Role of Tumor Necrosis Factor Alpha Blockade in the Treatment of Congestive Heart Failure / Lisman KA, Stetson SJ, Koerner MM, Farmer JA, Toore-Amione G. / Congest Heart Fail. 2002; 8(5): 275-9.

The Importance of Tumor Necrosis Factor and Lipoproteins in the Pathogenesis of Chronic Heart Failure / Sharma R, Al-Nasser FO, and Anker SD / Heart Fail Monit. 2001:2(2):42-7.

Cardiac Myocyte Necrosis Induced by Angiotensis II / Lip-Bun Tan, Jorge E. Jalil, Ruth Pick, Joseph S. Janicki and Karl T. Weber / Circulation Research vol. 69, No. 5, Nov. 1991 pp. 1185-1195.

The Adrenergic Nervous System In Heart Failure / Michael R. Bristow, M.D. / The New England Journal of Medicinevol. 311 No. 13 Sep. 27, 1984 pp. 850-851.

Negative Inotropic Effects of Cytokines on the Heart Mediated by Nitric Oxide / Mitchell S. Finkel, Carmine V. Oddis, Timothy D. Jacob, Simon C. Watkins, Brack G. Hattler and Richard L. Simmons / Science vol. 257 Jul. 17, 1992 pp. 387-389.

Immunoregulatory Feedback Between Interleukin-1 and Glucocorticoid Hormones / H. Besedovsky, A. Del Rey, E. Sorkin, and C. Dinarello / Science vol. 233 Aug. 8, 1986 pp. 652-654.

Role of vagus nerve signaling in CNI 1493-mediated suppression of acute inflammation / L. Borovikova, S. Ivanova, D. Nardi, M. Zhang, H Yang, M. Ombrellino and K. Tracey / Elsevier Science B.V. Atuonomic Neuroscience: Basic and Clinical 85 (2000) 141-147.

Cellular Basis for the Negative Inotropic Effects of Tumor Necrosis Factor-β in the Adult Mamalian Heart / T. Yokoyama, L. Vaca, R. Rossen, W. Durante, P Hazarika and D. Mann / The Journal of Clinical Investigation, Inc. / vol. 92, Nov. 1993, 2303-2312.

Cytokines and Cardiomyocyte Death / Kari J. Pulkki / 1997 The Finnish Medical Society DUODECIM, Ann Med 29, 339-343.

Subdiaphragmatic vagotomy suppressed endotoxin-induced activation of hypothalamic corticotropin-releasing hormone neurons and ACTH secretion / R.P.A. Gaykema, I. Dukstra, and F.J.H. Tilders / Endocrinologyvol. 136, No. 10 pp. 4717-4720.

Interleukin 1 and tumor necrosis factor inhibit cardiac myocyte β-adrenergic responsiveness / T. Gulick, M.K. Chung, S.J. Pieper, L.G. Lange, and G.F. Schreiner / Proc. Natl. Acad. Sci vol. 86 pp. 6753-6757, Sep. 1989 Medical Sciences.

Mechanisms and Models In Heart Failure A Combinatorial Approach / D.L. Mann, MD / Circulation 1999: 100:999-1008.

Proteomics of heart disease / Em McGregor and M.J. Dunn / Human Molecular Genetics, vol. 12, Review Issue 2 2003 R135-R144.

Geriatric Cachexia: the role of cytokines [1,2] Shing-Shing Yeh and Michael W. Schuster / Am J. Clin Nutr 1999, 70:183-197.

Thermogenic and corticosterone response to intravenous cytokines (IL-1β and TNF-α) are attenuated by subdiaphragmatic vagotomy / M. Fleshner, L.E. Goehler, B.A. Schwartz, M. McGorry, D. Martin, S.F. Maier, and L.R. Watkins / Journal of Neuroimmunology / Elesevier Science B.V. 86 (1998) 134-141.

Implications of Immune-to-brain communicatin for sickness and pain / L.R. Watkins and S.F. Maier / Proc. Natl. Acad. Sci vol. 96, pp. 7710-7713, Jul. 1999.

Loss of a gp130 Cardiac Muscle Cell Survival Pathway Is a Critical Event in the Onset of Heart Failure during Biomechanical Stress / H. Hirota, J. Chen, U.A.K. Betz, K. Rajewsky, Y. Gu, J. Ross, Jr., W. Muller and K. R. Chien / Cell. vol. 97 189-198 Apr. 16, 1999.

Vagus nerve stimulation attenuates the systemic inflammatory response to endotoxin / L.V. Borovikova, S. Ivanova, M. Zhang, H. Yang, G.I. Botchkina, L.R. Watkins, H. Wang, N. Abumrad, J.W. Eaton and K.J. Tracey / Nature vol. 405 May 25, 2000 pp. 458-462.

Efferent Vagal Fibre Stimulation Blunts Nuclear Factor-κB Activation and Protects Against Hypovolemic Hemorrhagic Shock / S. Guarini, Ph.D; D. Altavilla, Ph.D; MM Cainazzo, MD; D. Giuliani, Ph.D; A. Bigiani, Ph.D; H. Marini, MD; G. Squadrito, MD; L. Minutoli, MD; A. Bertolini, MD; R. Marini, Ph.D.; E.B. Adamo, MD; F.S. Venuti, MD; and F. Squadrito, MD / Circulation Mar. 4, 2003 pp. 1189-1194.

Myocardial extracellular matrix remodeling in transgenic mice overexpressing tumor necrosis factor α can be modulated by anti-tumor necrosis factor α therapy / Y.Y. Li; Y.Q. Feng; T. Kadokami; C.F. McTiernan; R. Draviam; S.C. Watkins; and A.M. Feldman / PNAS Nov. 7, 2000 vol. 97 No. 23 pp. 12746-12751.

Tumor Necrosis Factor Alpha-induced Apoptosis in Cardiac Myocytes Involvement of the Sphingolipid Signaling Cascade in Cardiac Cell Death / K.A. Krown; M. Trevor Page; C. Nguyen; D. Zechner; V. Gutierrez; K.L. Comstock; C.C. Glembotski; P. J.E. Quintana; and R.A. Sabbadini / J. Clin. Invest. vol. 98 No. 12, Dec. 1996, 2854-2865.

New Therapeutics For Chronic Heart Failure / D.L. Mann; A. Deswal; B. Bozkurt; and G. Torre-Amione / Annu. Rev. Med. 2002 53:59-74.

Tumor Necrosis Factor-α Provokes a Hypertrophic Growth Response in Adult Cardiac Myocytes / T. Yokoyama, MD; M. Nakano, MD, PhD; J.L. Bednarczyk, PhD; B.W. McIntyre, PhD; M. Entman, MD; D.L. Mann, MD / Circulation 1997; 95:1247-1252.

US 6,184,239, 02/2001, Puskas (withdrawn)

METHOD AND SYSTEM FOR VAGAL NERVE STIMULATION WITH MULTI-SITE CARDIAC PACING

CROSS-REFERENCE TO RELATED APPLICATIONS

This application is a continuation-in-part of U.S. application Ser. No. 10/207,725 filed Jul. 29, 2002, now U.S. Pat. No. 6,718,208, which is a continuation-in-part of U.S. application Ser. No. 09/670,441 filed Sep. 26, 2000, now U.S. Pat. No. 6,449,507, which is a continuation-in-part of U.S. application Ser. No. 09/433,323 filed Nov. 3, 1999, now U.S. Pat. No. 6,266,564, which is a continuation of U.S. application Ser. No. 09/070,506 filed Apr. 30, 1998, now U.S. Pat. No. 6,006,134, which is a continuation-in-part of U.S. application Ser. No. 08/640,013 filed Apr. 30, 1996, now abandoned, and is also a continuation-in-part of U.S. application Ser. No. 10/421,459, filed Apr. 23, 2003, now U.S. Pat. No. 6,904,318, which is a continuation of U.S. application Ser. No. 09/669,961, filed Sep. 26, 2000, now abandoned, the disclosures of which are incorporated herein by reference.

FIELD OF THE INVENTION

This invention relates to methods and systems for modulating inflammatory processes and vasodilation in patients with chronic heart failure, especially a procedure that includes multi-site pacing of the heart. More particularly, this invention relates to methods and systems for vagal nerve stimulation in combination with multi-site pacing.

BACKGROUND OF THE INVENTION

Despite major advances in the prevention and treatment of cardiovascular diseases, as is evident from the substantial decline in mortality due to acute myocardial infarction and strokes in the United States and in most European countries, national statistics indicate that the incidents and prevalence of congestive heart failure (CHF) have been increasing in recent years. Patients with CHF have an impaired quality of life and a shortened life expectation. CHF is defined generally as the inability of the heart to deliver enough blood to the peripheral tissues to meet metabolic demands. Although angiotensin-converting enzymes (ACE) inhibitors have been shown to modify the natural course of CHF reducing the mortality rate by 30%, the underlying disease continues to evolve, becoming progressively unresponsive to common drugs, until eventually intravenous inotropic support is needed. At end-stage, heart transplantation becomes the only therapeutic option.

It has been suggested that heart failure progresses as a result of the over-expression of biologically active molecules that are capable of exerting toxic effects on the heart and circulation (Bristow, 1984; Tan et al, 1991; Dunn 2003). Furthermore, several studies have demonstrated that congestive heart failure (CHF) patients are characterized by persistent immune activation (Damas et al., 2001). In fact, many aspects of the syndrome of heart failure, for example, left ventricular dysfunction, pulmonary edema, cardiomyopathy, endothelial dysfunction, anorexia and cachexia, can be-caused by the biological effects of pro-inflammatory cytokines resulting from persistent activation of surrounding cells. Secondly, the pattern of expression of pro-inflammatory mediators is very similar to that observed with the classical neurohormones such as angiotensin II and norepinephrine that are believed to play an important role in the progression of heart failure (Mann, 1999). Together, these findings support the rationale for targeting inflammatory mediators, or cytokines, in heart failure.

Inflammation is often induced by pro-inflammatory cytokines, such as tumor necrosis factor (TNF), interleukin (IL)-1$\alpha$, IL-1 $\beta$IL-6, IL-8, IL-18, interferon$\gamma$, platelet activating factor (PAF), macrophage migration inhibitory factor (MIP), and other compounds (Thompson, 1998-book). These factors are produced by a variety of different cell types, most importantly immune cells but also non-immune cells such as smooth muscle cells and neurons (Yeh & Schuster, 1999). Pro-inflammatory cytokines contribute to a variety of diseases through their release which often results in an inflammatory cascade of both cellular and systemic events. Mammals respond to and regulate inflammatory cascades in part through nervous system regulation, (Besedovsky et al., 1986; Gaykema et al., 1995; Fleshner et al., 1998; Watkins and Maier, 1999)

Pro-inflammatory cytokines such as TNF$\alpha$ and IL-1$\beta$ modulate cardiovascular functions by a variety of mechanisms. For example, cytokines can depress myocardial contractility (Yokokyam et al., 1993; Gulick et al., 1989; Finkel et al., 1992), induce cardiomyocyte hypertrophy and itersitial fibrosis (Yokoyama et al., 1997; Hirota et al., 1999) and promote cardiomyocyte apoptosis and collagen production (Krown et al. 1996; Pulkki, 1997; Li et al., 2000). Interestingly, TNF, IL-1$\beta$and IL-6 are expressed in direct relation to worsening New York Heart Association (NYHA) functional classification (Diwan et al., 2003). In addition, there is increasing evidence that many of the conventional therapies for heart failure may work, at least in part, through the modulation of pro-inflammtory cytokines. For example, administration of angiotensin type-1 receptor antagonists and/or $\beta$1-selective adrenergic antagonists lead to decreases in circulating levels of inflammatory mediators in patients with heart failure.

Traditional therapies for treating heart failure include the administration of ACE inhibitors and/or vasodilators. More recently, agents designed to reduce inflammation, for example, enfliximab-Remicade, etanercept-Enbrel, pentoxifylline, intravenous immunoglubulin, have been used in combination with the traditional therapies with mixed results.

Therapies aimed solely at reducing the pro-inflammatory mediator TNF, e.g., enfliximab-Remicade and etanercept-Enbrel, have resulted in negative clinical trials. Two large pivotal trials were halted early due to a lack of improvement with treatment (RECOVER and RENAISSANCE for etanercept). A third study investigating the use of enfliximab was stopped due to an increased incidence of mortality and hospitalization for worsening CHF. Although successful in the treatment of rheumatoid arthritis and Crohn's, these agents are known to be intrinsically toxic to the heart. Additionally, their mechanism of action is not sufficient to reduce cardiac inflammation.

While the rationale for targeting the pro-inflammatory cascade in heart failure is well established, current therapies have failed to target pro-inflammatory mediators with agents that can be safely used in the context of heart failure. Additionally, these failed attempts suggest that targeting a single component (ie cytokine) of the inflammatory cascade may not be sufficient in a disease as complex as heart failure. Instead, an approach that harnesses more higher order functions, such as the nervous system's ability to regulate inflammatory functions, may be more effective in modulating the entire inflammatory cascade.

Recently it has been shown that electrical stimulation of the vagus nerve is capable of ameliorating immune activation (Borovikova et al., 2000; Guarini et al., 2003) and is therefore useful in inhibiting inflammatory cytokine cascades that mediate several disease conditions. This discovery is based on the finding that treatment of a pro-inflammatory cytokine producing cell with a cholinergic agonist attenuates the release of pro-inflammatory cytokines from that cell (Borovikova et al., 2000a-Nature and Boroviokova et al., 2000b-Auton Neurosci). Subsequent findings demonstrated that electrical stimulation of the vagus nerve fibers causes the release of acetylcholine which acts on the pro-inflammatory cytokine producing cells in-vivo to attenuate an inflammatory response. Stimulation of the vagus nerve is capable of reducing the exacerbated pro-inflammatory immune response induced by endotoxin or hemorrhagic shock. The significant body of evidence demonstrating sustained expression of pro-inflammatory cytokines produces detrimental effects in the heart suggests that vagal nerve stimulation may ameliorate these effects. In addition, cardiac vagal activity is diminished in chronic heart failure.

Vagal nerve stimulation increases vagal tone, which produces antiarrythmic effects and vasodilation. Depending on the chosen location of stimulation, vagal stimulation may exert beneficial effects in CHF in addition to modulating the pro-inflammatory response. For example, vagal stimulation increases the density of cardiac noradernergic plexuses, increase cardiac blood supply and improve ventricular contractility (Zamotrinsky, 2001). In the present invention, stimulation of the vagus to modulate the inflammatory response during pacing of the heart may also operate through other pathways to restore autonomic balance.

A number of proposals have been proposed to target specific cytokines and/or the entire inflammatory cascade to treat congestive heart failure through biologics and pharmaceutical means as described in detail in U.S. Pat. Nos. 6537540, 5998386, 6221851, 6572895, 5977408 and 6589954 all incorporated herein by reference. The medical literature also discloses treatment strategies to inhibit pro-inflammatory cytokines (Diwan et al., 2003; MacGowan and McNamara, 2002; Damas et al., 2001; Greenberg et al., 2001; Francis, 1998), all incorporated herein by reference. These approaches have focused predominately on inhibiting single cytokines rather than targeting the broad inflammatory cascade of events. The negative clinical trials demonstrate that the past treatment strategies aimed at inhibiting pro-inflammatory cytokines did not demonstrate clinical benefit for patients with CHF. It appears that an effective immuno-modulation strategy in the heart must target pre-translational (intracellular) TNF rather than soluble/cell surface TNF, as well as the more broad inflammatory cascade.

Vagus nerve stimulation (VNS) targets pro-inflammatory agents at the requisite point in their exacerbation, making VNS a useful strategy to resist cardiac inflammation. For example, PCT patent application no. WO 01/89526, incorporated herein by reference, discloses a method of electrically stimulating the efferent vagal nerve to inhibit the pro-inflammatory cytokine cascade to treat congestive heart failure.

Stimulation of the vagus nerve has been proposed to control various heart rate functions in patients suffering from heart failure. For example, U.S. Pat. No. 6,473,644 discloses stimulating the vagus nerve to modulate heart rate and U.S. Pat. No. 5,203,326 discloses an anti-arrhythmia pacemaker wherein electrical stimulation is delivered to a patient's vagal cervical ganglion, both incorporated herein by reference.

In the normal human heart, the sino-atrial (SA) node, generally located near the junction of the superior vena cava and the right atrium, constitutes the primary natural pacemaker initiating rhythmic electrical excitation. The cardiac impulse arising from the SA node is transmitted through the atrial conduction pathways of Bachmann's bundle and inter-nodal tracts at the atrial level, thereby causing the two atrial chambers to contract. The contraction of the atrial chambers pumps blood from those chambers into the respective ventricular chambers. The excitation impulse is further transmitted to the ventricles through the atrio-ventricular (AV) node, and via a conduction system comprising the Bundle of His, or Common Bundle, the right and left bundle branches, and the Purkinje fibers. In response, the ventricles contract, the right ventricle pumping unoxygenated blood through the pulmonary artery to the lungs and the left ventricle pumping oxygenated blood through the aorta and arterial tree throughout the body. Disruption of this natural pacing and conduction system as a result of aging or disease is often successfully treated by artificial cardiac pacing using an implantable pulse generator, from which rhythmic electrical pulses are applied to the heart at a desired rate. One or more heart chambers may be electrically paced depending on the location and severity of the conduction disorder, see U.S. Patent Publication No. 2001/0049543, incorporated herein by reference.

A common type of intra-atrial conduction defect is known as intra-atrial block (IAB), a condition where the atrial activation is delayed in getting from the right atrium (RA) to the left atrium (LA). In left bundle branch block (LBBB) and right bundle branch block (RBBB), the activation signals are not conducted in a normal fashion along the right or left bundle branches respectively. Thus, in a patient with bundle branch block, the activation of the ventricle is slowed, and the QRS is seen to widen due to the increased time for the activation to traverse the conduction path.

In patients suffering from CHF, the right and left heart chambers may not contract in synchrony with each other. In such cases, cardiac output deteriorates because the contractions of the right and left heart chambers are not synchronized sufficiently to pump blood. It is believed that cardiac output can be significantly improved when left and right chamber synchrony is restored. In fact, clinical investigation performed on patients who suffer from heart failure (i.e., inability of the heart to pump the required amount of blood) indicates that for a certain subset of these patients simultaneous stimulation of the left and right ventricles may be advantageous.

In the cardiac cycle, a P wave of a patient's electrocardiogram (ECG) is produced by a depolarization of the atrial fibers just before they contract, and, when the cardiac impulse reaches the ventricular fibers to stimulate them into depolarization, a QRS complex is produced just before contraction of the ventricular walls. This is followed by a T wave which is indicative of the electrical activity occurring upon repolarization of the ventricular fibers. Simultaneous stimulation of the left and right ventricles can be beneficial therapy to patients whose ECG displays a marked desynchronization in contraction of the two ventricular chambers. In such cases, it is observed that after a right ventricular stimulation, considerable time may elapse for the cardiac impulse to travel from the apex of the right ventricle through the septum and to the free wall of the left ventricle, with the septum contracting earlier than the latter. Consequently, the mechanical forces of the ventricular contraction are less favorable for an effective hemodynamic output in such patients. The duration or width of the QRS complex may increase because of an injury to the Purkinje fibers that inhabit and stimulate the ventricular septum and the lateral ventricular walls, and which could therefore increase the time for the impulse to spread throughout the ventricular walls. Patients who display a lack of ventricular synchronization primarily exhibit a wide QRS complex indicative of a bundle branch block—generally a LBBB.

A number of proposals have been proposed for providing pacing therapies to restore synchronous depolarization and contraction of a single heart chamber or right and left, upper and lower, heart chambers as described in detail in U.S. Pat. Nos. 5,403,356, 5,797,970, 5,902,324, 5,720,768 and 5,792,203 all incorporated herein by reference. The proposals appearing in U.S. Pat. Nos. 3,937,226, 4,088,140, 4,548,203, 4,458,677, 4,332,259 are summarized in U.S. Pat. Nos. 4,928,688 and 5,674,259, all incorporated herein by reference. The advantages of providing sensing in addition to pacing in both the right and left heart chambers is addressed in patents 4,928,688 and 5,674,259, as well as in U.S. Pat. Nos. 4,354,497, 5,174,289, 5,267,560, 5,514,161, and 5,584,867, also all incorporated herein by reference.

The medical literature also discloses a number of approaches of providing multi-chamber pacing as set forth in: Daubert et al., "Permanent Dual Atrium Pacing in Major Intra-atrial Conduction Blocks: A Four Years Experience", PACE (Vol. 16, Part II, NASPE Abstract 141, p. 885, April 1993); Daubert et al., "Permanent Left Ventricular Pacing With Transvenous Leads Inserted Into The Coronary Veins", PACE (Vol. 21, Part II, pp. 239-245, January 1998); Cazeau et al., "Four Chamber Pacing in Dilated Cardiomyopathy", PACE (Vol. 17, Part II, pp. 1974-1979, November 1994); and Daubert et al., "Renewal of Permanent Left Atrial Pacing via the Coronary Sinus", PACE (Vol. 15, Part II, NASPE Abstract 255, p. 572, April 1992), Cazeau et al., PACE (Vol. 17, November 1994, Part II, pp. 1974-1979), all incorporated herein by reference.

In addition to the above-mentioned disclosures concerning the advantages of substantially simultaneous or synchronous pacing of the two ventricles, it is known that there is an advantage to synchronous pacing of the left atrium and the right atrium for patients with IAB. The advantage of synchronous pacing of the two atria for patients with IAB was disclosed at AHA 1991, Abstract from 64th Scientific Sessions, "Simultaneous Dual Atrium Pacing in High Degree Inter-Atrial Blocks: Hemodynamic Results", Daubert et al., No. 1804. Further, it is known that patients with IAB are susceptible to retrograde activation of the left atrium, with resulting atrial tachycardia. Atrial resynchronization through pacing of the atria can be effective in treating the situation. PACE, Vol. 14, April 1991, Part II, p. 648, "Prevention of Atrial Tachyarrythmias Related to Inter-Atrial Block By Permanent Atrial Resynchronization", Mabo et al., No. 122. For patients with this condition, a criterion for pacing is to deliver a left atrial stimulus before the natural depolarization arrives in the left atrium.

Since the stimulation of the vagus nerve appears to have the desired effect of simultaneously reducing inflammation by targeting multiple components of the inflammatory cascade, VNS in combination with bi-ventricular pacing may provide an improvement to the current therapies for treating and/or managing the multi-faceted syndromes of chronic heart failure. Therefore, it is desirable to provide methods and systems for controllably stimulating the vagus nerve in combination with multi-site pacing of the heart for treating heart failure.

SUMMARY OF THE INVENTION

The present invention preferably comprises an external pulse generator or an implantable pulse generator (IPG), a nerve stimulator and a pacing lead system, preferably employing right and left heart, atrial and/or ventricular leads. In accordance with one embodiment of the present invention, a method and apparatus is provided to stimulate the vagus while synchronizing the right and left chambers of the heart. It should be appreciated that the present invention may be utilized particularly to treat patients suffering CHF.

The present invention may comprise a multi-lead system utilizing sensing, e.g., impedance sensing, for determining optimum cardiac parameters, e.g., pacing parameters for pacing the left ventricle so that left heart output is maximized. Sensing may also be used for determination of arrhythmias or progression of heart failure. The leads of the present invention may comprise one or more stimulating, pacing and/or defibrillating electrodes. The leads may be unipolar and/or bipolar.

The present invention may comprise one or more stimulation leads capable of directly or indirectly stimulating the vagus nerve. One or more electrodes of the one or more stimulation leads may be placed at one or more preferable positions along the vagus, or the branches of the vagus, e.g., in the cardiac plexus, or placed in the trachea, in the esophagus, or in a artery and/or vein. Stimulation of the vagus may be performed in combination with the delivery of one or more cardiac agents.

The present invention may comprise a pulse generator capable of delivering electrical pulses to multiple electrodes independent of each other. The present invention may comprise one or more sensors, e.g., a biological sensor to determine the level of a pro-inflammatory cytokine and/or a sensor for detecting an abnormal event in the heart. The one or more sensors may sense one or more parameters including the patient's electrogram (ECG), heart rate and/or rhythm, status of rest, exercise or activity of the patient (e.g., using an accelerometer), etc., the latter enabling the device to provide a rate adaptive response, as well as other dysrhythmia correction therapies. The one or more sensors may include one or more conventional sensors for sensing physiological signals for detecting congestive heart failure, for example. The present invention may be used to deliver a closed loop therapy. In one embodiment of the present invention, an implantable cardio-defibrillator (ICD) may be used.

The present invention includes a method of performing a medical procedure, comprising: positioning a first stimulation electrode in a first position to stimulate a first portion of cardiac tissue; positioning a second stimulation electrode in a second position to stimulate a second portion of cardiac tissue; positioning a third stimulation electrode in a third position to stimulate a nerve; providing stimulation energy to the first stimulation electrode to stimulate the first portion of cardiac tissue to contract; providing stimulation energy to the second stimulation electrode to stimulate the second portion of cardiac tissue to contract in synchrony with the first portion of cardiac tissue; and providing stimulation energy to the third stimulation electrode to stimulate the nerve. One or more electrodes may be positioned, for example, through a thoracotomy, a sternotomy, or a percutaneous incision, e.g., in a torso of a patient, in a leg of a patient, in an arm of a patient, or in a neck of a patient. One or more sensors may be used.

The present invention includes a method of performing a medical procedure, comprising: providing stimulation energy from a cardiac stimulator to a first stimulation electrode to stimulate a first portion of cardiac tissue; providing stimulation energy from the cardiac stimulator to a second stimulation electrode to simultaneously stimulate a second portion of cardiac tissue; and providing stimulation energy from a nerve stimulator to a third stimulation electrode to stimulate a vagal nerve.

The present invention includes a system for performing a medical procedure, comprising; an implantable nerve stimulator for delivering stimulation energy to one or more nerve stimulation electrodes; and an implantable cardiac stimulator in communication with the nerve stimulator for delivering stimulation energy to two or more stimulation electrodes.

The present invention includes a device for performing a medical procedure comprising: a processor; one or more nerve stimulation electrodes operatively connected to the processor; two or more cardiac stimulation electrodes operatively connected to the processor; and one or more physician operated switches operatively connected to the processor to allow a physician to regulate stimulation output from the one or more nerve stimulation electrodes and the two or more cardiac stimulation electrodes.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
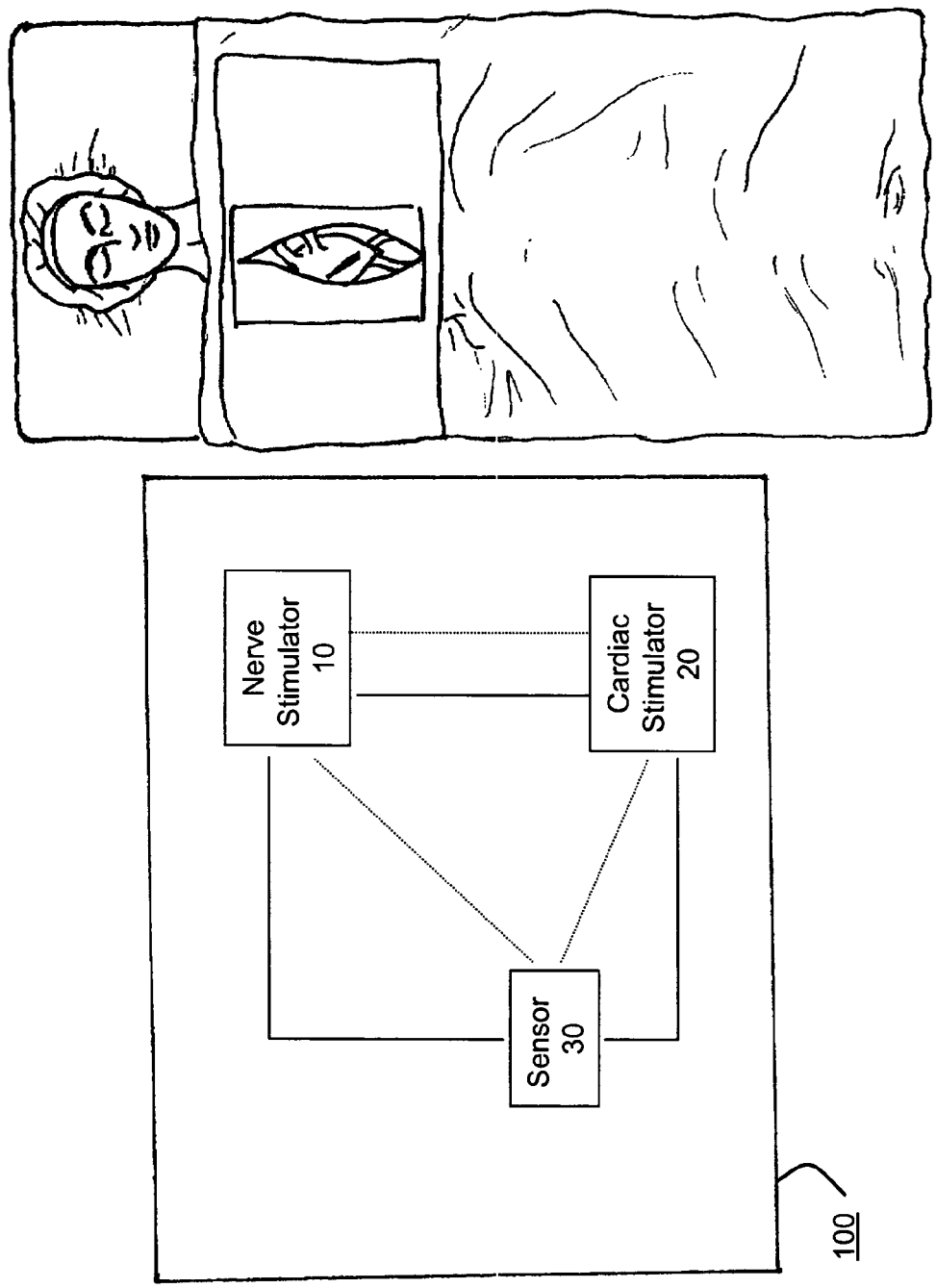
FIG. 1 is a schematic view of one embodiment of a system for performing a medical procedure in accordance with the present invention.

In a bi-ventricular pacing system, an implantable pulse generator (IPG) is generally coupled to the right chamber, e.g., via a right chamber lead, and the left chamber, e.g., via a left chamber lead, to enable simultaneous pacing of both right and left chambers to reduce the width of the QRS complex of the patient's cardiac activity to a more normal duration. The left chamber lead is typically placed in the coronary sinus of the heart. This lead may be used for both pacing and sensing in the left ventricle (LV) of the heart. The right chamber lead is typically positioned in the right ventricle (RV) of the heart and may be used for both pacing and sensing in the right ventricle.

In one embodiment of the present invention, a right atrial lead, a left atrial lead, a right ventricular lead, and/or a left ventricular lead may be coupled to a pulse generator for example in a conventional manner. The pulse generator may be programmable. The pulse generator, for example an IPG, may include a telemetry transceiver of a type known in the pacing art. The pulse generator may comprise a microcomputer circuit and a pacing circuit. The pacing circuit may include a digital controller/timer circuit, an output amplifiers circuit, and a sense amplifiers circuit, as well as a number of other circuits and components. In embodiment of the present invention, an implantable device or an external device having capabilities of pacing, cardioversion and/or defibrillation may be used.

In one embodiment of the invention, the leads may comprise one or more pacing and/or sensing electrodes or one or more electrodes that may be used for both pacing and sensing functions. The "pace/sense" electrodes may be selected to be used exclusively as pace or sense electrodes or to be used in common as pace/sense electrodes in programmed combinations for sensing cardiac signals and delivering pacing pulses. Separate or shared indifferent pace and sense electrodes can also be designated in pacing and sensing functions.

Impedance sensors may be used in pacing systems for obtaining information concerning cardiac function. For example, U.S. Pat. No. 5,501,702, incorporated herein by reference, discloses making impedance measurements from different electrode combinations. In such system, a plurality of pace/sense electrodes are disposed at respective locations, and different impedance measurements are made on a time/multiplexing basis. As set forth in the referenced patent, the measurement of the impedance present between two or more sensing locations is referred to "rheography." A rheographic, or impedance measurement involves delivering a constant current pulse between two "source" electrodes, such that the current is conducted through some region of the patient's tissue, and then measuring the voltage differential between two "recording" electrodes to determine the impedance therebetween, the voltage differential arising from the conduction of the current pulse through the tissue or fluid between the two recording electrodes. The referenced patent discloses using rheography for measuring changes in the patient's thoracic cavity; respiration rate; pre-ejection interval; stroke volume; and heart tissue contractility. U.S. Pat. No. 4,303,075, incorporated by reference, discloses a system for measuring impedance between a pair of electrodes connected to or in proximity with the heart, and processing the variations of sensed impedance to develop a measure of stroke volume.

In one embodiment of the present invention, one or more defibrillation leads or coils may be used in one or more chambers of the heart. Under typical defibrillator implant conditions, a coil on a lead is introduced into a ventricle to serve as one electrode or pole, and the defibrillator case or can that houses the batteries, capacitors, electronic components and circuitry may be used as the second pole for the current path during the defibrillation shock. Alternatively, an atrial defibrillation coil may be inserted on a lead into an atrium to enable stimulation of the atrial chamber, as appropriate, with pacing pulses and for application of defibrillating shocks. Alternatively, defibrillation coils may be placed in both ventricles. In this case, when the coils are energized simultaneously the coil in the left ventricle may be the anode and the coil in the right ventricle may be the cathode. Alternatively, the ventricular defibrillation coils may constitute a single defibrillation pole and are energized simultaneously as an anode, and the metal case or can constitutes a second defibrillation pole which is energized together with the defibrillation coils as a cathode.

In one embodiment of the present invention, biventricular pacing, e.g., "cross-chamber" configurations, may be used with vagal nerve stimulation. Both the right ventricle (RV) and the left ventricle (LV) may be paced simultaneously in a cross-chamber configuration. Sensing may also be performed in a cross-chamber configuration. For example, impedance sensing may be carried out across any combination of the four heart chambers, e.g., right atrium vs. left atrium; right ventricle vs. left ventricle; right atrium vs. left ventricle; and left atrium vs. right ventricle. Impedance measurements between these combinations of chambers can be carried out for purposes of analyzing and confirming arrhythmias, including fibrillation, and changes in conduction patterns, as seen in the morphology of such impedance measurements, which can be monitored and processed for making determinations of progression of heart failure. Thus, cross-measurements of RA-LV and LA-RV can be useful in obtaining histories to determine changes indicating progression of heart failure.

In one embodiment of the present invention, the distal end of an LV lead may be advanced endocardially through the superior vena cava, the right atrium, the ostium of the coronary sinus (CS), the CS, and into a coronary vein descending from the CS to locate the distal end of the LV lead at a desired LV site. Typically, left ventricular coronary sinus leads do not employ any fixation mechanism and instead rely on the close confinement within the coronary vessels to maintain the one or more electrodes at the distal end of the LV lead at a desired site. The LV lead may be unipolar or bipolar. In a bipolar lead design the distal end of the lead comprises two electrodes while the unipolar lead design comprises one electrode. In the unipolar embodiment, the second or indifferent electrode may be an implantable pulse generator (IPG) can. The one or more electrodes of the LV lead may be used for both stimulation and sensing. Alternatively, the distal end of an LV lead may be placed on the epicardial surface of the heart.

In one embodiment of the present invention, the distal end of an RV lead may be advanced endocardially through the superior vena cava, the right atrium, and into the RV chamber to locate the distal end of the RV lead therein. The distal end of the lead may be attached to the right ventricle wall of the heart, for example the apex, by one or more attachment mechanisms. The attachment mechanism for the RV lead may, for example, comprise a screw for screwing the lead into the wall of the heart or it may comprise one or more tines or it may comprise some other attachment mechanism known in the art. The RV lead may be unipolar or bipolar. In a bipolar lead design the distal end of the lead comprises two electrodes while the unipolar lead design comprises one electrode. In the unipolar embodiment, the second or indifferent electrode may be an IPG can. The one or more electrodes of an RV lead may be used for both stimulation and sensing.

In one embodiment of the present invention, a RA lead may be used. The distal end of an RA lead may be passed endocardially through the superior vena cava into the right atrium of the heart. The distal end of the lead may be attached to the right atrial wall of the heart by one or more attachment mechanisms. The attachment mechanism may, for example, comprise a screw for screwing the lead into the wall of the heart or it may comprise one or more tines. A number of attachment mechanisms for attaching leads to tissues are known in the art. The RA lead may be unipolar or bipolar. In a bipolar lead design the distal end of the lead comprises two electrodes while the unipolar lead design comprises one electrode. In the unipolar embodiment, the second or indifferent electrode may be an IPG can. The one or more electrodes of an RA lead may be used for both stimulation and sensing.

In one embodiment of the invention, a device includes a right ventricular pacing lead with an electrode positioned to stimulate the right ventricle, a left ventricular pacing lead with an electrode positioned to stimulate the left ventricle and means for applying stimulating pacing pulses to the right and left ventricular pacing leads for stimulating the ventricles simultaneously.

FIG. 1 shows a schematic view of one embodiment of a system for performing a medical procedure in accordance with the present invention at 100. System 100 comprises a nerve stimulator 10, and a cardiac stimulator 20. System 100 may also feature a sensor 30.

In one embodiment, the nerve stimulator 10 may be used to electrically modulate inflammatory processes and cause vasodilation in patients, e.g., patients with chronic heart failure, by stimulating the vagus nerve. In one embodiment, the cardiac stimulator 20 may be used to electrically pace the heart, e.g., multi-site pacing of the heart. Vagal stimulation, alone or in combination with multi-site pacing, may be used to treat heart failure.

It is known that stimulation of the vagus nerve can reduce the sinus rate, as well as prolong AV conduction time or, if stimulation energies are high enough, induce AV node block. Use of vagal nerve stimulation to treat supraventricular arrhythmias and angina pectoris is disclosed in the article "Vagal Tuning" by Bilgutay et al., Journal of Thoracic and Cardiovascular Surgery, Vol. 56, No. 1, July, 1968, pp. 71-82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in California Medicine, Vol. 112, pp. 41-50, March, 1970. It is also known that stimulation of the vagus nerve is capable of ameliorating immune activation (Borovikova et al., 2000; Guarini et al., 2003).

As set forth in "Functional Anatomy of the Cardiac Efferent Innervation" by Randall et al., in Neurocardiology, edited by Kulbertus et al, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node", Bluemel et al., Am. J. Physiol. 259, (Heart Circ. Physiol. 28) H1504-H1510, 1990, stimulation of the fat pad associated with the SA node results in slowing of the sinus rate without the accompanying prolongation of AV conduction time which normally results from vagal nerve stimulation. The article also indicates that stimulation of the fat pad associated with the AV node is believed to produce corresponding effects limited to the AV node, i.e., extension of the AV conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, January, 1980, pp. 48-57, the fat pads associated with both the AV node and the SA node may be stimulated by means of electrodes located in the right pulmonary artery. The results obtained include both a depression of the sinus rate and a prolongation of the AV conduction time in response to continuous stimulation at 2-80 Hz at up to 50 ma.

Generally in healthy individuals, the SA node functions as the pacemaker. Normal heart rhythm associated with the SA node is typically referred to as sinus rhythm. When the SA node fails, the AV node generally takes over creating a heart rate of approximately 35 to 60 beats per minute. Heart rhythm associated with the AV node is typically referred to as nodal rhythm. When the AV node itself is blocked or injured, a new even slower pacemaker site may form at the junction of the AV node and the His bundle. Heart rhythm associated with this junction is typically referred to as junctional escape rhythm. When this junction site is inhibited, the Purkinje fibers in the His bundle or below may act as a pacemaker creating a heart rate of approximately 30 beats per minute. Heart rhythm associated with the Purkinje fibers is typically referred to as idioventricular rhythm.

Nerve stimulator 10 may be powered by AC current, DC current or it may be battery powered either by a disposable or re-chargeable battery. Nerve stimulator 10 may be combined in a single unit with a switch box. Nerve stimulator 10 may comprise one or more surgeon controlled switches 250 (see FIG. 2). The switches may be, for example, a hand switch, a foot switch, or a voice-activated switch comprising voice-recognition technologies.

Nerve stimulator 10 may be slaved to cardiac stimulator 20 or cardiac stimulator 20 may be slaved to nerve stimulator 10. Nerve stimulator 10 may be implantable.

Cardiac stimulator 20 may be a conventional ventricular demand pacer or a multi-site pacer, e.g., a multi-chamber pacer such as an atrial-ventricular pacer. Cardiac stimulator 20 may comprise the capabilities of pacing, cardioversion and/or defibrillation. Cardiac stimulator 20 may be powered by AC current, DC current or it may be battery powered either by a disposable or re-chargeable battery. Cardiac stimulator 20 may be any conventional pacing device suitable for ventricular demand pacing and having leads electrically coupled to a switch box. Cardiac stimulator 20 may be combined in a single unit with a switch box. Cardiac stimulator 20 may comprise one or more surgeon controlled switches 260. The switches may be, for example, a hand switch, a foot switch, or a voice-activated switch comprising voice-recognition technologies. A single switch may be used to regulate both cardiac stimulator 20 and nerve stimulator 10. Cardiac stimulator 20 and nerve stimulator 10 may be combined in a single housing or can.

Sensor 30 may be any suitable blood gas sensor for measuring the concentration or saturation of a gas in the blood stream. For example, sensor 30 may be a sensor for measuring the concentration or saturation of oxygen or carbon dioxide in the blood. Alternatively, sensor 30 may be any suitable sensor for measuring blood pressure or flow, for example a Doppler ultrasound sensor system, or a sensor for measuring hematocrit (HCT) levels. Alternatively sensor 30 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

Sensor 30 may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

Sensor 30 may be used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, temperature, pressure, components of metabolic processes, chemical concentrations, for example, the absence or presence of specific peptides, proteins, enzymes, gases, ions, etc.

Sensor 30 may include one or more imaging systems, camera systems operating in UV, visible, or IR range; electrical sensors; voltage sensors; current sensors; impedance sensors, piezoelectric sensors; electromagnetic interference (EMI) sensors; photographic plates, polymer-metal sensors; charge-coupled devices (CCDs); photo diode arrays; chemical sensors, electrochemical sensors; pressure sensors, sound wave sensors; magnetic sensors; UV light sensors; visible light sensors; IR light sensors; radiation sensors; flow sensors; temperature sensors; or any other appropriate or suitable sensor. Sensor 30 may be an implantable sensor or an external sensor, a continuous, in-line monitoring system or it may be attached to an extracorporeal device.

In one embodiment of the invention, sensor 30 may be a cerebral blood flow sensor, in which case, the sensor may be placed in any suitable manner for sensing cerebral blood flow. For example, sensor 30 may be inserted between the skull and the dura of the brain. Alternatively, sensor 30 may be placed in the patient's neck. For example, at least a portion of sensor 30 may be placed in an artery, such as the carotid artery. Placement of sensor 30 in the carotid artery would allow measurement of blood as it flows to the brain. Alternatively, sensor 30 may be placed in a vein, such as the jugular vein. Placement of sensor 30 in the jugular vein would allow measurement of blood as it flows from the brain.

In the case of blood oxygen saturation sensing, a certain level of oxygen generally remains in the blood as it flows from the brain. This level may be established by measuring the patient's oxygen prior to surgery. If blood measured by sensor 30 in the vein has oxygen below the established level, the brain is consuming all or most of the oxygen flowing to it and probably requires additional oxygen. Other suitable placements of sensor 30 may be possible. Sensor 30 may be used to alert a surgeon to changes in the patient's physiological condition.

Sensor 30 may be combined with cardiac stimulator 20 and/or nerve stimulator 10 in an implantable or external housing or can. Cardiac stimulator 20 and/or nerve stimulator 10 may be slaved to sensor 30. Sensor 30 may be powered by AC current, DC current or it may be battery powered either by a disposable or re-chargeable battery.

Sensor 30, nerve stimulator 10 and/or cardiac stimulator 20 may include one or more audible and/or visual signals or gauges 270 used to prepare or alert a surgeon to a change in the patient's condition. Sensor 30, nerve stimulator 10 and/or cardiac stimulator 20 may be slaved to a robotic system or a robotic system may be slaved to sensor 30, nerve stimulator 10 and/or cardiac stimulator 20. Computer—and voice-controlled robotic systems that position and maneuver endoscopes and/or other surgical instruments for performing microsurgical procedures such as anastomoses through small incisions may be used by a surgeon to perform precise and delicate maneuvers. These robotic systems may allow a surgeon to perform a variety of microsurgical procedures including endoscopic CABG. Endoscopic CABG may allow multiple occluded coronary arteries to be bypassed without a thoracotomy or mini-thoracotomy. Heart valve repair and replacement may also be other surgical applications for these robotic systems. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

Figure 2:
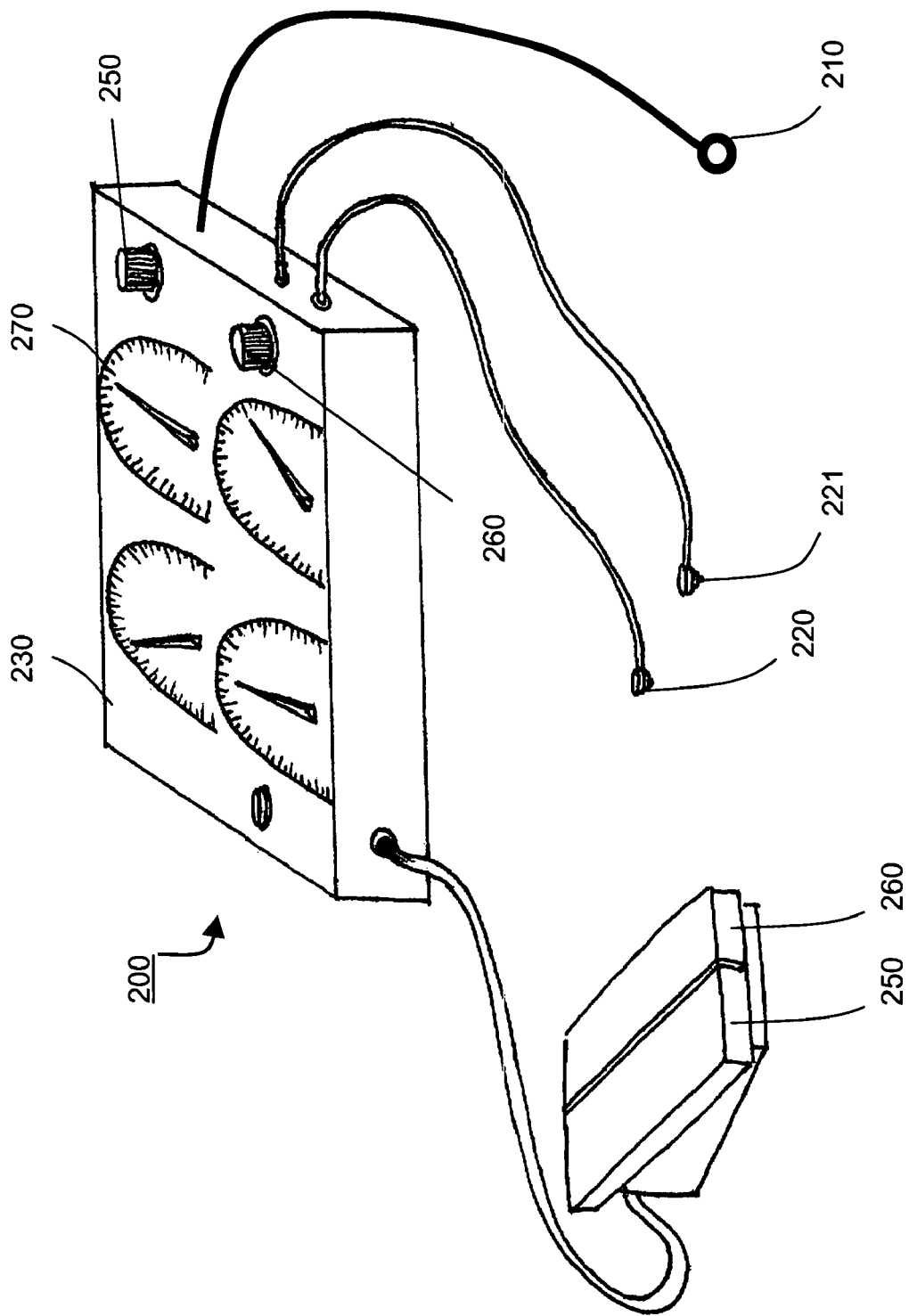
FIG. 2 is a schematic view of one embodiment of a medical device in accordance with the present invention.

FIG. 2 shows one embodiment of the present invention at 200. In this embodiment, the elements named above may be combined or connected to a control unit along with other components. The unit 200 may be used to coordinate the various elements. Unit 200 may incorporate a controller or any suitable processor 230.

Unit 200 may incorporate a nerve stimulator. For example, FIG. 2 shows an electrode for nerve stimulation at 210. Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes 210 may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present invention may include various electrodes, catheters and/or electrode catheters suitable for vagal nerve stimulation to temporarily stop or slow the beating heart and/or to control the inflammatory cascade. Vagal nerve stimulation may be performed alone or in combination with the delivery of one or more cardiac agents.

Nerve stimulation electrodes may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon which may be inflated with air or liquid to press the electrodes firmly against the vessel wall. Similar techniques may be performed by insertion of a catheter-type device into the trachea or esophagus. Additionally, tracheal tubes and esophageal tubes comprising electrodes may be used.

An electrode on a catheter-type device, for example, may be inserted into a vein in an arm of a patient via a percutaneous incision. The electrode may then be pushed up into the patient's subclavian vein. The subclavian vein crosses the vagal nerve near the first rib. Therefore, an electrode positioned in the subclavian vein of the patient can be positioned adjacent the vagus nerve.

Nerve stimulation electrodes may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters which incorporate one or more tunnels or passageways.

In one embodiment of the present invention, the location of the electrodes 210 is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues. In one embodiment of the present invention, the location of the electrodes 210 is chosen to elicit maximum control or modulation of one or more components of the immune system.

Unit 200 may also incorporate a cardiac stimulator. For example, FIG. 2 shows two electrodes for stimulation of the heart at 220 and 221. Cardiac stimulation electrodes used to stimulate the heart may be, for example, non-invasive, e.g., clips, or invasive, e.g., needles or probes. Cardiac stimulation electrodes may be positioned through a thoracotomy, sternotomy, endoscopically through a percutaneous port, through a stab wound or puncture, through a small incision in the chest, placed on the chest or in combinations thereof. The present invention may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes.

Controller 230 may be used to gather information from nerve stimulation electrodes 210 and cardiac stimulation electrodes 220 and 221. Controller 230 may also be used to control the stimulation levels and stimulation duration of nerve stimulation electrodes 210 and cardiac stimulation electrodes 220 and 221. Controller 230 may also gather and process information from the various components of system 100. This information may be used to adjust stimulation levels and stimulation times of nerve stimulation electrodes 210 and cardiac stimulation electrodes 220.

Figure 3:
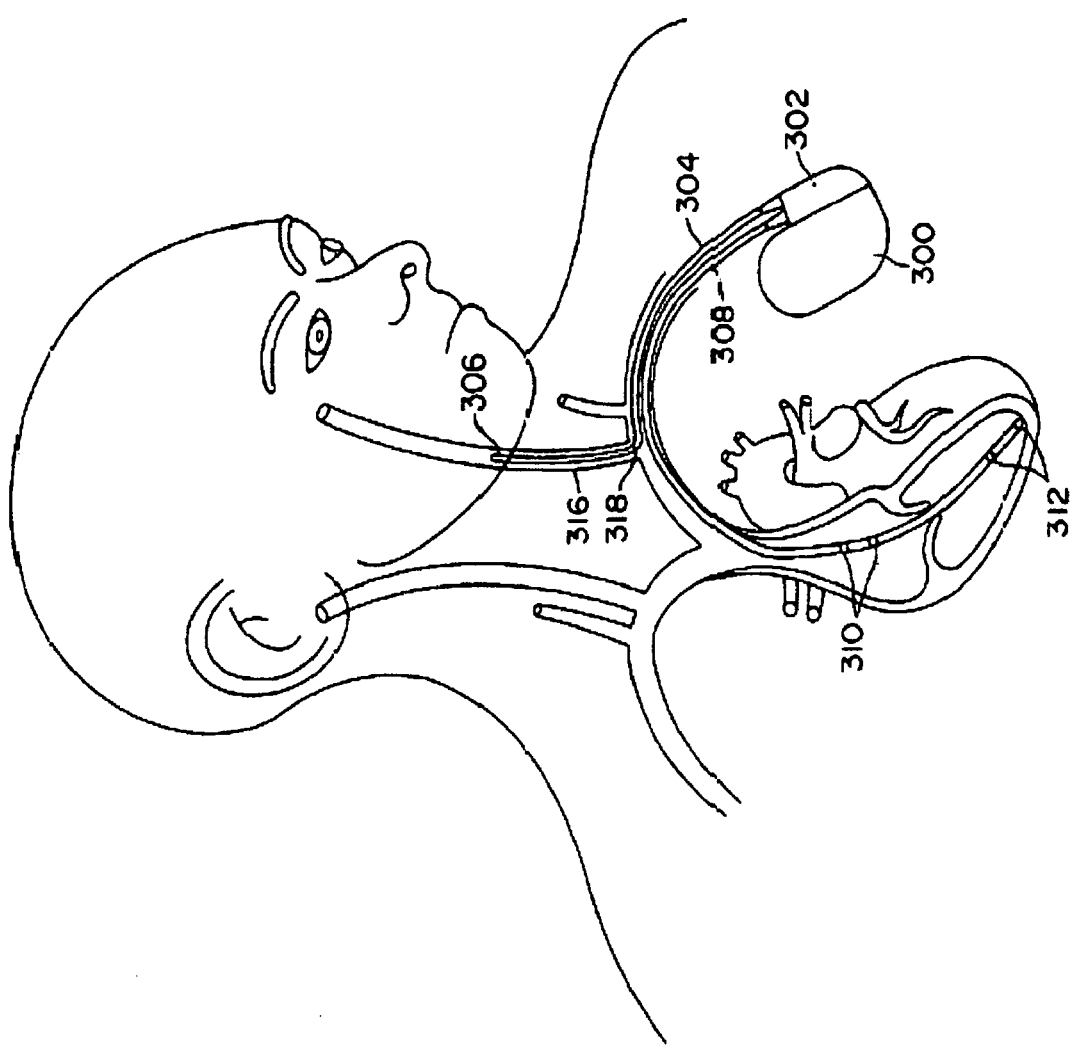
FIG. 3 is a schematic view of one embodiment of a medical device in accordance with the present invention.

FIG. 3 shows one embodiment of the present invention, wherein the elements named above may be combined or connected to an implantable control unit along with other components. Unit 300 may incorporate a controller or any suitable processor. Unit 300 is shown coupled to an electrode lead 304 used to stimulate the vagal nerve in accordance with the present invention. Unit 300 is also shown coupled to a second electrical lead 308, which, like electrical lead 304 is coupled to the circuitry within the housing of unit 300 by means of a connector block 302. As shown in FIG. 3, implantable unit 300 may include a multi-chamber cardiac stimulator and a nerve stimulator. Electrode lead 304 may include one or more nerve stimulation electrodes, as discussed above, located at or adjacent its distal end 306 which is shown positioned within the internal jugular vein 316. Nerve stimulation electrodes of electrode lead 304 are positioned so as to direct the stimulation pulses provided by the electrodes to the vagal nerve. Electrode lead 308 may include a pair of cardiac stimulation electrodes 310 capable of sensing and pacing the atrium of the patient's heart and a pair of cardiac stimulation electrodes 312 for sensing and pacing the ventricle of the patient's heart. Electrode lead 304 may be formed with a bend 318, preformed into the body of the lead a distance from the distal end of the lead 306 to position it appropriately for vagal nerve stimulation. The lead may be inserted and positioned generally according to the procedure disclosed in U.S. Pat. No. 5,354,318 issued to Taepke, describing a similarly located and configured lead, also incorporated herein by reference in its entirety.

Figure 4:
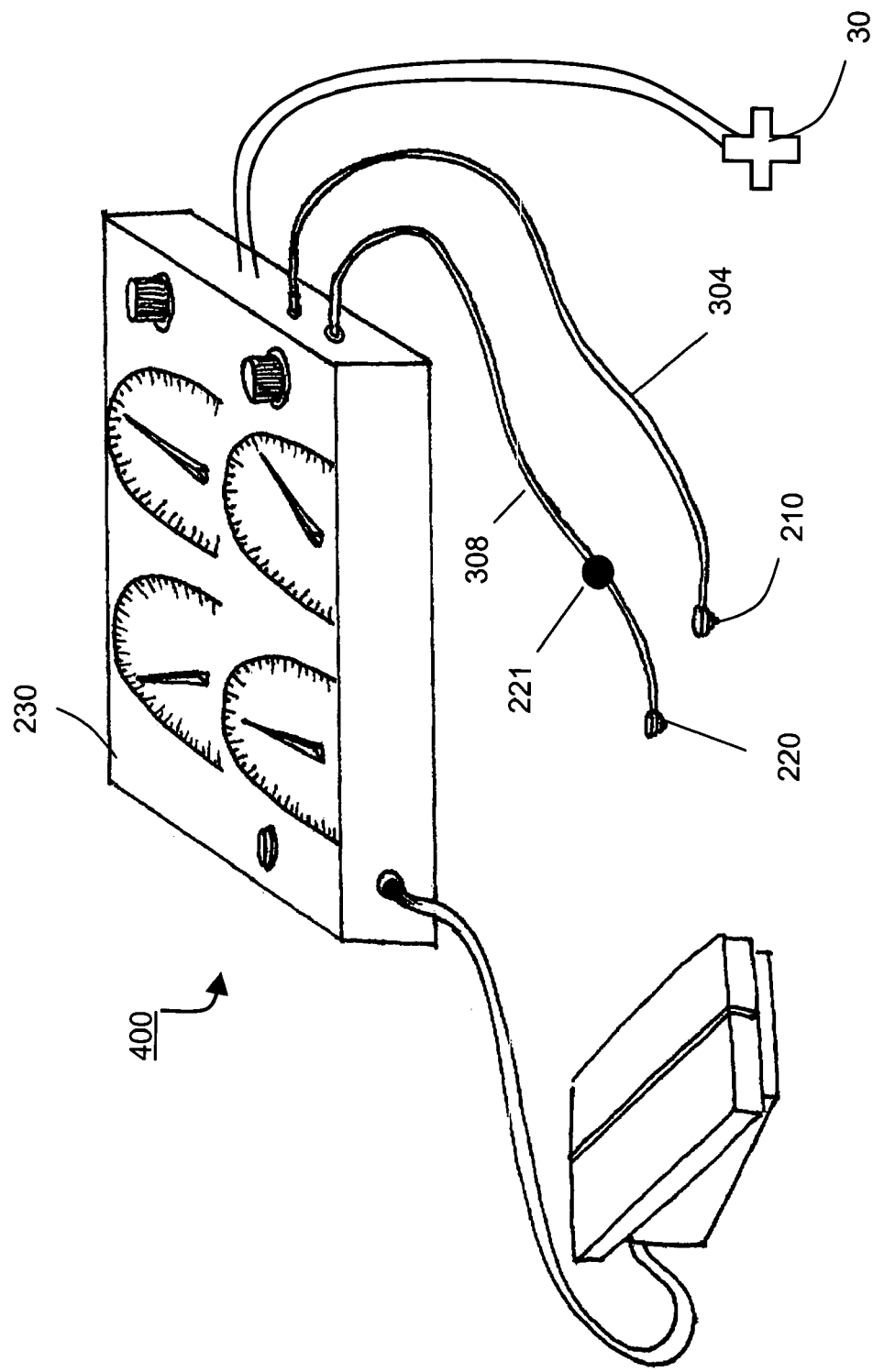
FIG. 4 is a schematic view of one embodiment of a medical device in accordance with the present invention.

FIG. 4 shows one embodiment of the present invention at 400. In this embodiment, unit 400 incorporates a nerve stimulator, a cardiac stimulator and a sensor 30. Unit 400 may incorporate a controller or any suitable processor 230. Unit 400 is coupled to an electrode lead 304 having a nerve stimulation electrode 210 at its distal end and to electrode lead 308 having cardiac stimulation electrodes 220 and 221.

Figure 5:
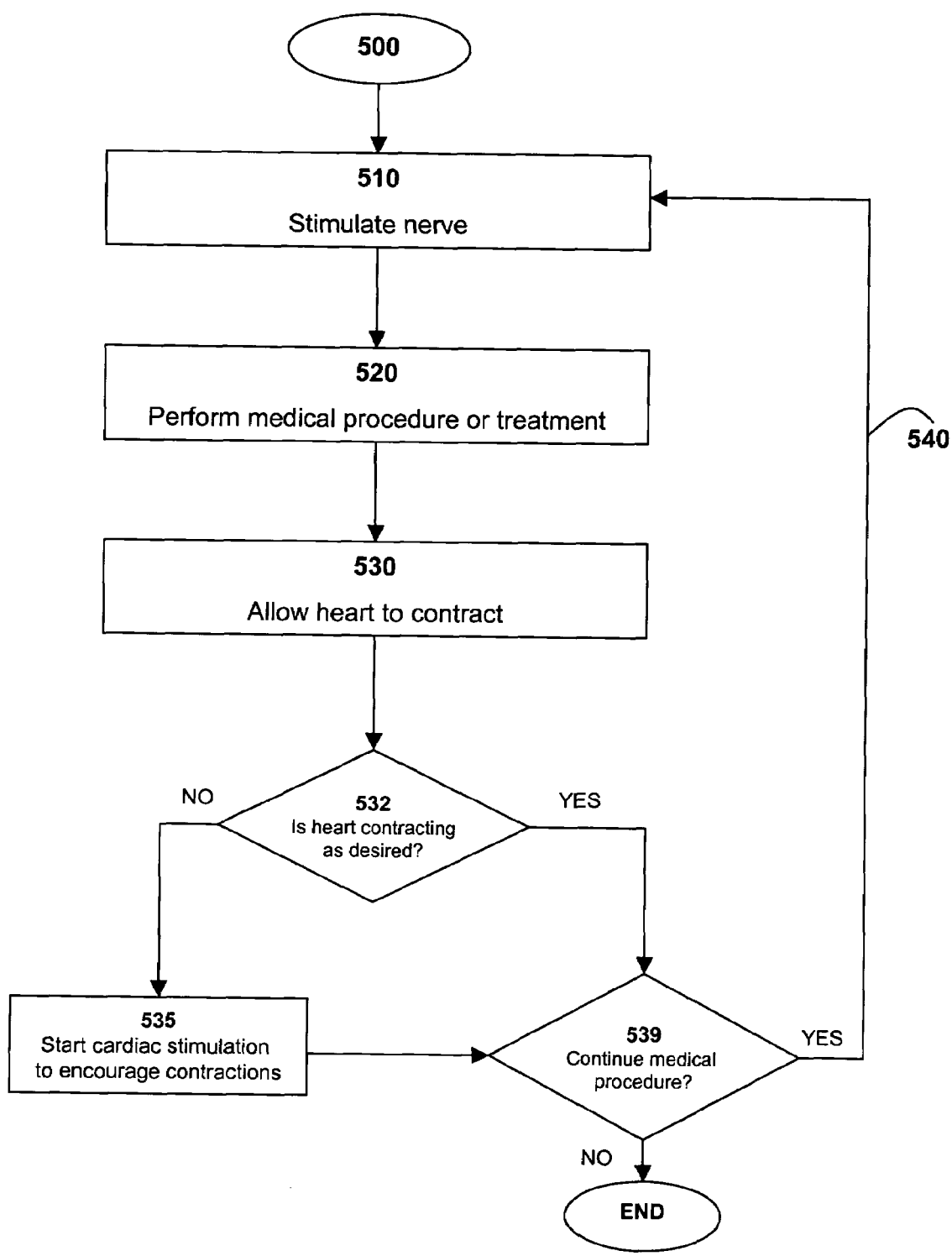
FIG. 5 is a flow diagram of one embodiment of a method of performing a medical procedure in accordance with the present invention.

FIG. 5 shows a flow diagram of one embodiment of the present invention. The patient is prepared for a medical procedure at 500. At block 510, a nerve that controls at least one component of the immune system is stimulated. Such a nerve may be for example a vagal nerve. During this time, one or more of a variety of pharmacological agents or drugs may be delivered and/or one or more physiological conditions of the patient may be sensed and monitored. The drugs may be administered for a variety of functions and purposes as described below. Drugs may be delivered or administered at the beginning of the procedure, intermittently during the procedure, continuously during the procedure, or following the procedure.

Drugs, drug formulations or compositions suitable for administration to a patient during a medical procedure may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

Drugs may be delivered via a drug delivery device that may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques.

Drugs may be delivered via an iontophoretic drug delivery device, for example placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the electrodes may also be used as nerve stimulation electrodes 210 or as cardiac stimulation electrodes 220 and/or 221.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential. The present invention may be combined with conventional CPB, the induced asystole as described by this invention may serve as a substitute for conventional cardioplegic arrest. For example, the combination of drugs and vagal stimulation may be used as a cardioplegic agent in a variety of medical procedures.

Other drugs, drug formulations and/or drug compositions that may be used according to this invention may include any naturally occurring or chemically synthesized anti-inflammatory agent. The term "anti-inflammatory agent" appearing herein may refer to one or more agents that reduce inflammation. Examples of anti-inflammatory agents include, but are not limited to, angiotensin-converting enzymes (ACE) inhibitors, angiotensin type-1 receptor antagonists, β1-selective adrenergic antagonists, enfliximab-Remicade, etanercept-Enbrel, pentoxifylline CDP571, CDP 870, D2E7, soluble TNF receptor Type I, pegylated soluble TNF receptor Type I, mediator-specific anti-inflammatory agents, activated protein C, non-steroidal anti-inflammatory drugs (NSAIDS) (ibuprofen, diclofenac, aspirin), corticosteroids (prednisone, methlyprednisone, betamethasone), cyclooxygenase inhibitors, RDP58, caspase inhibitors (z-VAD, Pralnacasan, VX-765, VX-799, CV1013, IDN 6556, IDN 6734, Activase, Retavase, TNKase, Pexelizumab, CAB2, RSR13), kinase inhibitors (CNI-1493, Gleevec, Herceptin, Iressa, imatinib, herbimycin A, tyrphostin47, and erbstatin, genistein, staurosporine, PD98059, SB203580, CNI-1493, VX-50/702, SB203580, BIRB 796, Glaxo P38 MAP Kinase inhibitor, RWJ67657, U0126,Gd, SCIO-469, RO3201195), NFkappa-B inhibitors (BMS345541, pyrrolidine dithiocarbamatem (PDTC) derivatives, SPC600839, nuclear translocation inhibitors, such as deoxyspergualin), phosphodiesterase IV inhibitors (Rolipram, Roflumilast, Arofylline, pentoxyfylline Ariflo, CDC-801, CD-7085, propenofylline), TACE inhibitors, HMGB-1 mA, and intravenous immunoglubulin.

Other drugs, drug formulations and/or drug compositions that may be used according to this invention may include any naturally occurring or chemically synthesized vasodilative agent. The term "vasodilative agent" appearing herein may refer to one or more agents that can dilate vessels. A vasodilative agent may comprise one or more vasodilative drugs in any suitable formulation or combination. Examples of vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine D1-like receptor agonist, stimulant or activator.

Other drugs, drug formulations and/or drug compositions that may be used according to this invention may include any naturally occurring or chemically synthesized vasoconstrictive agent. The term "vasoconstrictive agent" appearing herein may refer to one or more agents that can constrict vessels. The vasoconstrictive agent may comprise one or more suitable vasoconstrictive drugs in any suitable formulation or combination. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator.

Drugs, drug formulations and/or drug compositions that may be used during according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

In one embodiment, the cardiac asystole produced in accordance with the present invention is reversible, e.g., chemically such as by the administration of atropine or by natural forces. Beta-adrenergic stimulation or administration of calcium solutions may be used to reverse the effects of a calcium channel blocker such as verapamil. Agents that promote heart rate and/or contraction may be used in a preferred embodiment of the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

Typically, vagal nerve stimulation prevents the heart from contracting. This non-contraction must then be followed by periods without vagal nerve stimulation during which the heart is allowed to contract.

At Block 520, a medical procedure may be performed or begun. Such a procedure may be for example surgery on the heart. Alternatively, the procedure may be surgery performed on another organ of the body.

The term "medical procedure" may mean any one or more medical or surgical procedures such as, for example cardiac surgery, performed with or without cardiopulmonary bypass (CPB) circuits, heart valve repair, heart valve replacement, MAZE procedures, revascularization procedures, transmyocardial revascularization (TMR) procedures, percutaneous myocardial revascularization (PMR) procedures, CABG procedures, anastomosis procedures, non-surgical procedures, fluoroscopic procedures, beating heart surgery, vascular surgery, neurosurgery, brain surgery, electrophysiology procedures, diagnostic and therapeutic procedures, ablation procedures, ablation of arrhythmias, endovascular procedures, treatment of the liver, spleen, heart, lungs, and major blood vessels, treatment of heart failure, aneurysm repair, imaging procedures of the heart and great vessels, CAT scans or MRI procedures, pharmacological therapies, drug delivery procedures, gene therapies, cellular therapies, cancer therapies, radiation therapies, genetic, cellular, tissue and/or organ manipulation or transplantation procedures, coronary angioplasty procedures, placement or delivery of coated or noncoated stents, atherectomy procedures, atherosclerotic plaque manipulation and/or removal procedures, procedures where bleeding needs to be precisely controlled, procedures that require precise control of cardiac motion and/or bleeding.

When the medical procedure comprises one or more medical devices, e.g., coated stents, these devices may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized.

The medical procedure may be non-invasive, minimally invasive and/or invasive. The medical procedure may entail a port-access approach, a partially or totally endoscopic approach, a sternotomy approach or a thoracotomy approach. The medical procedure may include the use of various mechanical stabilization devices or techniques as well as various robotic or imaging systems.

In one method, the heart may be temporarily slowed or intermittently stopped for short periods of time to permit the surgeon to accomplish the required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers," Dec. 21, 1999, to inventors Hill and Junkman. This patent is assigned to Medtronic, Inc. and is incorporated herein by reference.

After a time, the medical procedure or one phase of the procedure is completed at 520. After some phase of the medical procedure is performed, cardiac contractions are allowed to occur (Block 530). Cardiac contractions may need to occur intermittently or continuously during the procedure or one phase of the procedure to ensure adequate blood flow. In one embodiment of the present invention, the stimulation from the nerve stimulator 10 is stopped or slowed enough to allow the heart to contract. In another embodiment of the present invention, the stimulation from the nerve stimulator 10 is continued while the heart is allowed to contract.

In another embodiment, the heart may be stimulated to ensure that cardiac contractions occur as desired (Block 535). For example, cardiac stimulator 20 may be used to apply pacing pulses to the heart at one or more sites to encourage the heart to contract normally. In particular, the pacing pulses may be applied to one or both ventricles as is well known in the field.

The present invention permits the heart to be stilled for selected and controllable periods of time in order to permit cardiac or other medical procedures to be performed. While such a period of stillness may be desired, it must not last too long, otherwise insufficient blood and oxygen is delivered to organs. Thus, it may be necessary to have the periods when the heart is beating (Blocks 530, 535).

If additional medical procedures or additional stages or phases of medical procedures need to be performed, the heart may again be stilled using the methods of stilling the heart described above. Therefore from Block 530 or Block 535, the method may be repeated (Block 540). For example, the heart may again be prevented from contracting by stimulation of the vagal nerve (Block 510) or stimulation of the vagal nerve may be continuous. Additional drugs may be delivered or the drugs previously administered may continue to be administered.

Additional surgery, additional steps in the medical procedure or additional medical procedures may again be performed (Block 520) and the heart may again be stimulated to encourage contractions (Block 535).

This cycle may be repeated until the procedure, such as a surgery or medical treatment, is completed. After the procedure is completed, step 535 may be performed until the heart is beating normally. At the procedure's end, one or more of a variety of pharmacological agents or drugs may be delivered or may continue to be delivered for example to alleviate pain or aid in recuperation. Other drugs may be administered for a variety of functions and purposes as described above.

For example, a surgical procedure at 520 may require several stitches to be made by the surgeon. The surgeon may stimulate the vagal nerve at 510 to stop the heart. Then the surgeon may make the first stitch at 520. The surgeon may then reduce or halt stimulation at 530 and allow the heart to contract. The surgeon may also pace the heart at 535. Then at 540, the surgeon may return to 510 to inhibit contractions of the heart. At 520, the surgeon will then make the second stitch. This process may be repeated (the loop designated by 540 may be repeated) until all the required stitches have been made.

Some medical procedures or treatments at 520 may require continuous stimulation of a nerve, e.g., in order to modulate one or more of patient's inflammatory processes.

Figure 6:
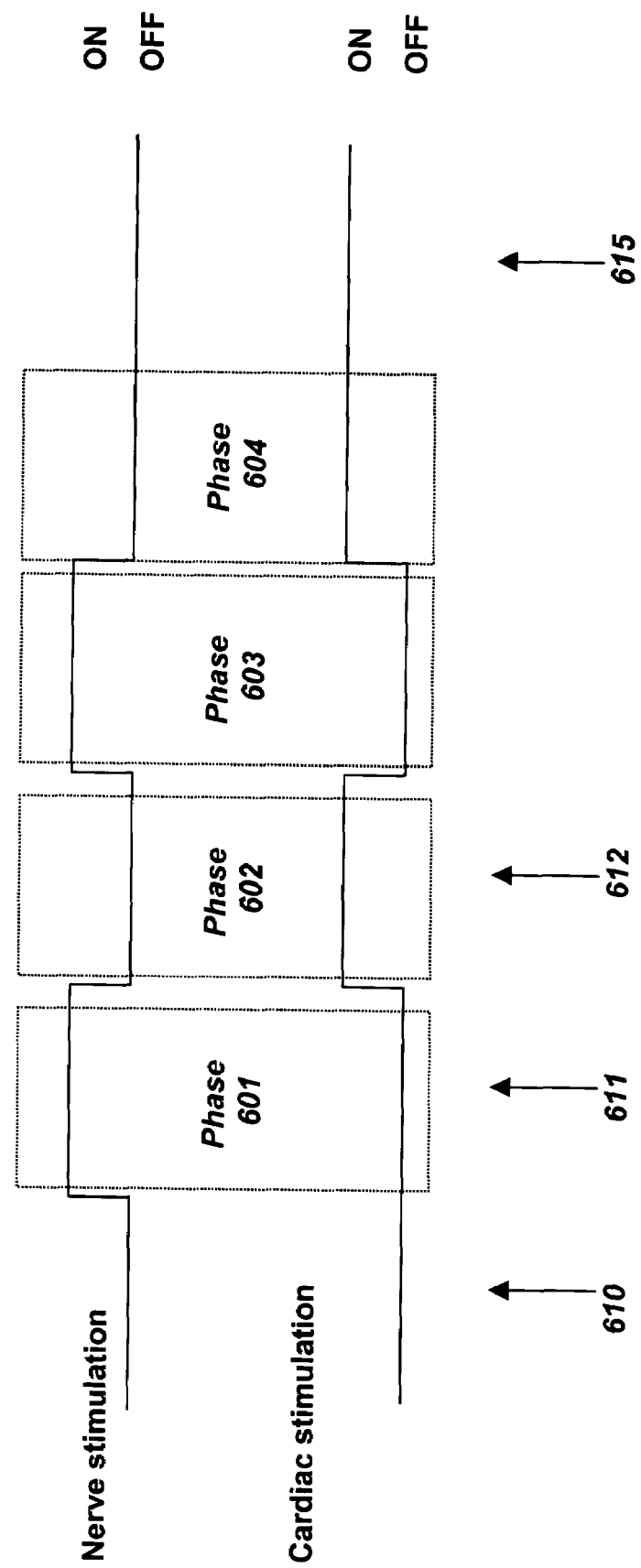
FIG. 6 is a timeline view of one embodiment of a system for controllably stopping or slowing a heart intermittently in accordance with the present invention.

FIG. 6 is a timeline showing the relation of the vagal nerve stimulation to the cardiac stimulation in one embodiment of the present invention.

Point 610 indicates a point before the medical procedure has begun. At this point 610, both nerve stimulation and cardiac stimulation are off. At point 610, the heart is beating regularly. Then nerve stimulation is turned on to inhibit beating of the heart. During phase 601, the vagal nerve stimulation is on and the cardiac stimulation is off. Point 611 is a representative point during phase 601. At point 611, the contractions of the heart are stilled or substantially slowed. Then during phase 602 the vagal stimulation is turned off and the cardiac stimulation may be turned on. Point 612 is a representative point during phase 602. At point 612, the contractions are allowed and/or may be induced. During phase 603, the vagal nerve stimulation is again turned on and the cardiac stimulation is turned off. Then during phase 604 the vagal stimulation is again turned off and the cardiac stimulation may again be turned on. The method of the present invention may be repeated as necessary until a point is reached, represented by point 615, when the necessary medical procedures are completed. At this point 615, nerve stimulation is off although cardiac stimulation may be left on in order to pace the heart to its normal rhythm.

Figure 7:
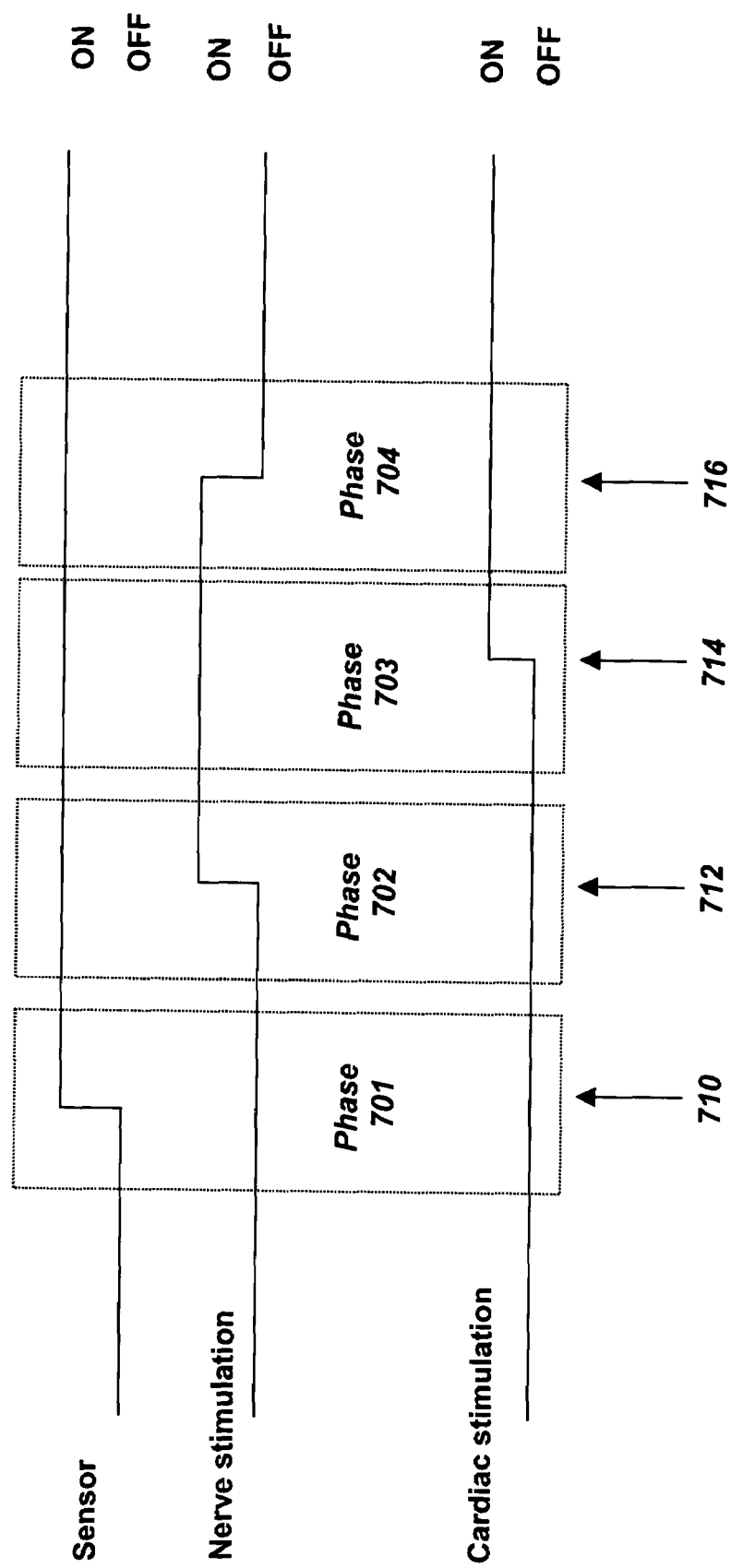
FIG. 7 is a timeline view of one embodiment of a system for stimulating a nerve while pacing a heart in accordance with the present invention.

FIG. 7 is a timeline showing the relationship of a sensor, a nerve stimulator and a cardiac stimulator in one embodiment of the present invention.

Point 710 is a representative point during phase 701. At point 710 both nerve stimulation and cardiac stimulation are off and a patient's state of inflammation, for example, may be monitored by a sensor. Thus, a sensor may be turned on at point 710. By the end of phase 701, sensing is on, nerve stimulation is off and cardiac stimulation is off.

Point 712 is a representative point during phase 702. At point 712, the patient's current state of inflammation may be determined to be greater than a particular level, for example. Since the state of inflammation at point 712 is greater than a particular level, nerve stimulation may be turned on. In one embodiment of the present invention, the amount of nerve stimulation may be adjusted based on the output of one or more sensors. By the end of phase 702, sensing is on, nerve stimulation is on and cardiac stimulation is off.

Point 714 is a representative point during phase 703. At point 714, cardiac stimulation may be turned on. In one embodiment of the present invention, a patient's heart may be stimulated or paced via multi-site stimulation or pacing. By the end of phase 703, sensing is on, nerve stimulation is on and cardiac stimulation is on.

Point 716 is a representative point during phase 704. At point 716, the patient's current state of inflammation may be determined to be less than a particular level, for example. Since the state of inflammation at point 716 is less than a particular level, nerve stimulation may be turned off. By the end of phase 704, sensing is on, nerve stimulation is off and cardiac stimulation is on.

Figure 8:
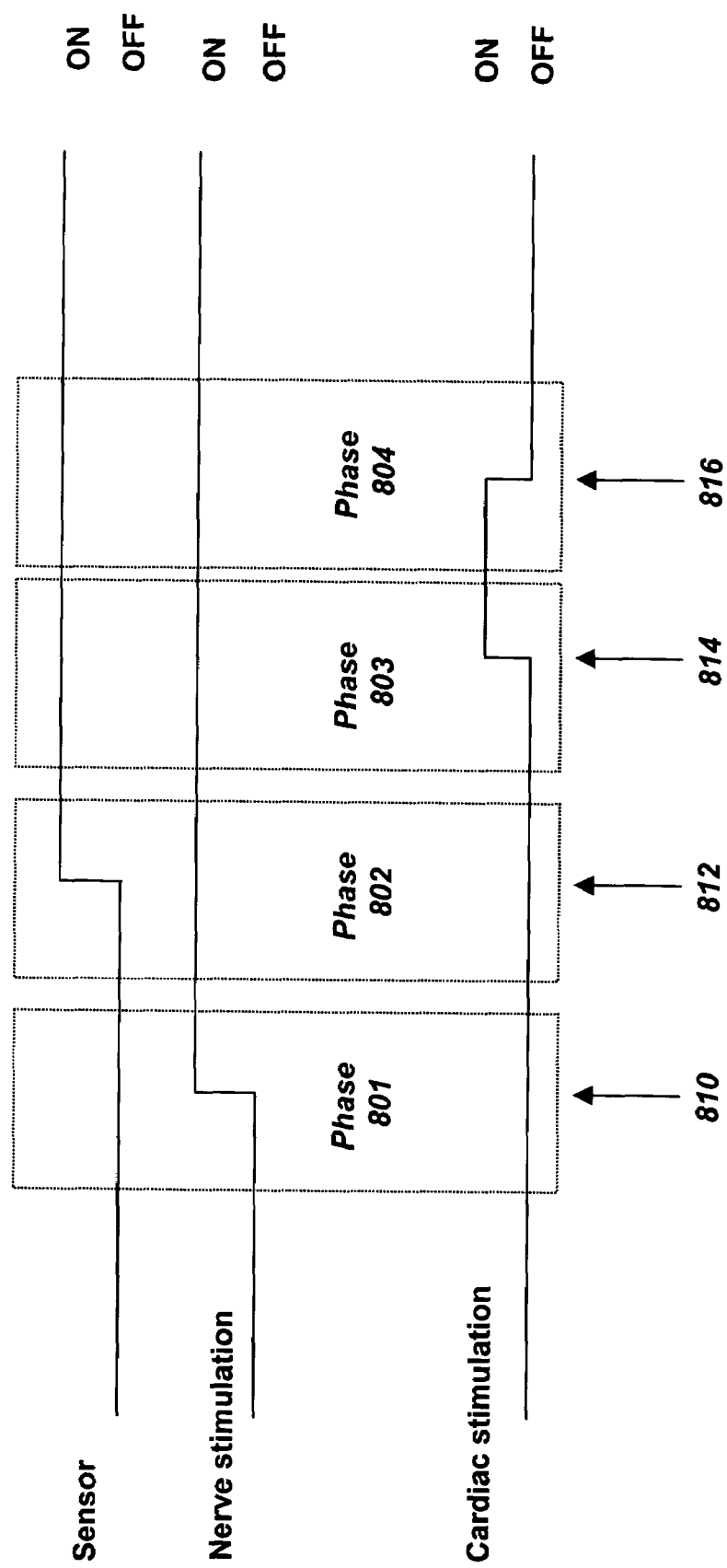
FIG. 8 is a timeline view of one embodiment of a system for stimulating a nerve while pacing a heart in accordance with the present invention.

FIG. 8 is a timeline showing the relationship of a sensor, a nerve stimulator and a cardiac stimulator in one embodiment of the present invention.

Point 810 is a representative point during phase 801. At point 810, nerve stimulation is turned on. By the end of phase 801, sensing is off, nerve stimulation is on and cardiac stimulation is off.

Point 812 is a representative point during phase 802. At point 812, a sensor is turned on to monitor the patient's cardiac contractions. By the end of phase 802, sensing is on, nerve stimulation is on and cardiac stimulation is off.

Point 814 is a representative point during phase 803. At point 814, the sensor may determine the patient's current state of cardiac contractions is insufficient, for example. Since the state of cardiac contractions is insufficient at point 814, cardiac stimulation may be turned on. In one embodiment of the present invention, the amount of cardiac stimulation may be adjusted based on the output of one or more sensors. In one embodiment of the present invention, cardiac stimulation may be single-site and/or multi-site stimulation, cardioversion and/or defibrillation. By the end of phase 803, sensing is on, nerve stimulation is on and cardiac stimulation is on.

Point 816 is a representative point during phase 804. At point 816, the patient's current state of cardiac contractions may be determined to be sufficient, for example. Since the state of cardiac contractions at point 816 is sufficient, cardiac stimulation may be turned off. By the end of phase 804, sensing is on, nerve stimulation is on and cardiac stimulation is off.

Figure 9:
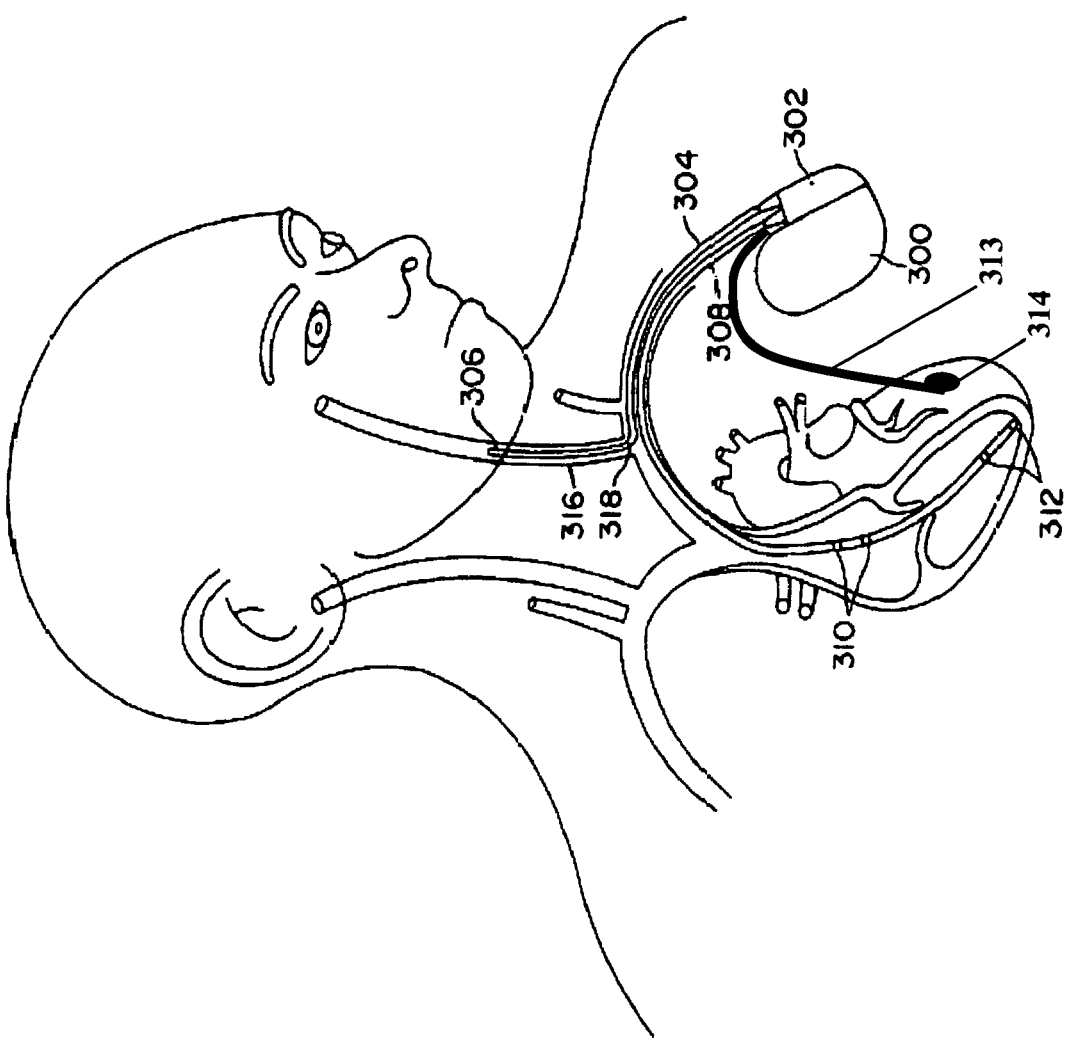
FIG. 9 is a schematic view of one embodiment of a medical device in accordance with the present invention.

FIG. 9 shows one embodiment of the present invention, wherein the elements named above may be combined or connected to an implantable control unit along with other components. Unit 300 may incorporate a controller or any suitable processor. Unit 300 is shown coupled to an electrode lead 304 used to stimulate the vagal nerve in accordance with the present invention. Unit 300 is also shown coupled to a second and third electrical lead 308 and 313, which, like electrical lead 304 are coupled to the circuitry within the housing of unit 300 by means of a connector block 302. As shown in FIG. 9, implantable unit 300 may include a multi-chamber cardiac stimulator and a nerve stimulator. Electrode lead 304 may include one or more nerve stimulation electrodes, as discussed above, located at or adjacent its distal end 306 which is shown positioned within the internal jugular vein 316. Nerve stimulation electrodes of electrode lead 304 are positioned so as to direct the stimulation pulses provided by the electrodes to the vagal nerve. Endocardial electrode lead 308 may include one or more cardiac stimulation electrodes 310 capable of sensing and/or pacing the atrium of the patient's heart and/or one or more cardiac stimulation electrodes 312 for sensing and/or pacing the right ventricle of the patient's heart. Epicardial electrode lead 313 may include one or more cardiac stimulation electrodes, as discussed above, located at or adjacent its distal end 314, which is shown positioned on the surface of the left ventricle of the patient's heart. Electrode lead 304 may be formed with a bend 318, preformed into the body of the lead a distance from the distal end of the lead 306 to position it appropriately for vagal nerve stimulation.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of performing a medical procedure, comprising:
   positioning a first stimulation electrode in a first position to stimulate a first portion of cardiac tissue, wherein the first stimulation electrode is positioned through a percutaneous incision;
   positioning a second stimulation electrode in a second position to stimulate a second portion of cardiac tissue;
   positioning a third stimulation electrode in a third position to stimulate a nerve;
   providing stimulation energy to the first stimulation electrode to stimulate the first portion of cardiac tissue to contract;
   providing stimulation energy to the second stimulation electrode to stimulate the second portion of cardiac tissue to contract in synchrony with the first portion of cardiac tissue; and
   providing stimulation energy to the third stimulation electrode to stimulate the nerve.

2. The method of claim 1 wherein the step of providing stimulation energy to the third stimulation electrode is coordinated with steps of providing stimulation energy to the first and second stimulation electrodes.

3. The method of claim 2 further comprising stimulating the nerve while stimulating the first and second portions of cardiac tissue.

4. The method of claim 1 wherein the first portion of cardiac tissue is at least a portion of a heart chamber.

5. The method of claim 4 wherein the heart chamber is a ventricle.

6. The method of claim 4 wherein the heart chamber is an atrium.

7. The method of claim 1 wherein the percutaneous incision is made in a torso of a patient.

8. The method of claim 1 wherein the percutaneous incision is made in a leg of a patient.

9. The method of claim 1 wherein the percutaneous incision is made in an arm of a patient.

10. The method of claim 1 wherein the percutaneous incision is made in a neck of a patient.

11. The method of claim 1 wherein the first position is an endocardial position.

12. The method of claim 1 wherein the third position is a subcutaneous position.

13. The method of claim 1 wherein a cardiac stimulator provides the stimulation energy to the first and second stimulation electrodes.

14. The method of claim 13 wherein the cardiac stimulator is an implantable cardiac stimulator.

15. The method of claim 1 wherein a nerve stimulator provides the stimulation energy to the third stimulation electrode.

16. The method of claim 15 wherein the nerve stimulator is an implantable nerve stimulator.

17. The method of claim 1 further comprising a sensor to detect a cardiac event.

18. The method of claim 17 wherein a cardiac stimulator in communication with the sensor provides the stimulation energy to the first and second stimulation electrodes.

19. A method of performing a medical procedure, comprising:
   positioning a first stimulation electrode in a first position to stimulate a first portion of cardiac tissue;
   positioning a second stimulation electrode in a second position to stimulate a second portion of cardiac tissue;
   positioning a third stimulation electrode in a third position to stimulate a nerve;
   providing stimulation energy to the first stimulation electrode to stimulate the first portion of cardiac tissue to contract;
   providing stimulation energy to the second stimulation electrode to stimulate the second portion of cardiac tissue to contract in synchrony with the first portion of cardiac tissue; and
   providing stimulation energy to the third stimulation electrode to stimulate the nerve, wherein the step of providing stimulation energy to the third stimulation electrode is coordinated with steps of providing stimulation energy to the first and second stimulation electrodes, and wherein the nerve is stimulated while stopping stimulation of the first and second portions of cardiac tissue.

20. A method of performing a medical procedure, comprising:
   positioning a first stimulation electrode in a first position to stimulate a first portion of cardiac tissue;
   positioning a second stimulation electrode in a second position to stimulate a second portion of cardiac tissue;
   positioning a third stimulation electrode in a third position to stimulate a nerve;
   providing stimulation energy to the first stimulation electrode to stimulate the first portion of cardiac tissue to contract;
   providing stimulation energy to the second stimulation electrode to stimulate the second portion of cardiac tissue to contract in synchrony with the first portion of cardiac tissue; and
   providing stimulation energy to the third stimulation electrode to stimulate the nerve, wherein the step of providing stimulation energy to the third stimulation electrode is coordinated with steps of providing stimulation energy to the first and second stimulation electrodes, and wherein the first and second portions of cardiac tissue are stimulated while stopping stimulation of the nerve.

21. The method of claim 20 wherein the nerve is a vagal nerve.

22. A method of performing a medical procedure, comprising:
   positioning a first stimulation electrode in a first position to stimulate a first portion of cardiac tissue;
   positioning a second stimulation electrode in a second position to stimulate a second portion of cardiac tissue;
   positioning a third stimulation electrode in a third position to stimulate a nerve;
   providing stimulation energy to the first stimulation electrode to stimulate the first portion of cardiac tissue to contract;
   providing stimulation energy to the second stimulation electrode to stimulate the second portion of cardiac tissue to contract in synchrony with the first portion of cardiac tissue;
   providing stimulation energy to the third stimulation electrode to stimulate the nerve; and
   delivering at least one drug during the medical procedure.

23. A method of performing a medical procedure, comprising:

positioning a first stimulation electrode in a first position to stimulate a first portion of cardiac tissue, wherein the first stimulation electrode is positioned through a thoracotomy;
positioning a second stimulation electrode in a second position to stimulate a second portion of cardiac tissue;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

24. A method of performing a medical procedure, comprising:
positioning a first stimulation electrode in a first position to stimulate a first portion of cardiac tissue, wherein the first stimulation electrode is positioned through a sternotomy;
positioning a second stimulation electrode in a second position to stimulate a second portion of cardiac tissue;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

25. A method of performing a medical procedure, comprising:
positioning a first stimulation electrode in a first position to stimulate a first portion of cardiac tissue, wherein the first position is an epicardial position;
positioning a second stimulation electrode in a second position to stimulate a second portion of cardiac tissue;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

26. A method of performing a medical procedure, comprising:
positioning a first stimulation electrode in a first position to stimulate a first portion of cardiac tissue, wherein the first position is a myocardial position;
positioning a second stimulation electrode in a second position to stimulate a second portion of cardiac tissue;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

27. A method of performing a medical procedure, comprising:
positioning a first stimulation electrode in a first position to stimulate a first portion of cardiac tissue, wherein the first position is a venous position;
positioning a second stimulation electrode in a second position to stimulate a second portion of cardiac tissue;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

28. A method of performing a medical procedure, comprising:
positioning a first stimulation electrode in a first position to stimulate a first portion of cardiac tissue, wherein the first position is an arterial position;
positioning a second stimulation electrode in a second position to stimulate a second portion of cardiac tissue;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

29. A method of performing a medical procedure, comprising:
positioning a first stimulation electrode in a first position to stimulate a first portion of cardiac tissue;
positioning a second stimulation electrode in a second position to stimulate a second portion of cardiac tissue, wherein the second stimulation electrode is positioned through a thoracotomy;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

30. A method of performing a medical procedure, comprising:
positioning a first stimulation electrode in a first position to stimulate a first portion of cardiac tissue;

positioning a second stimulation electrode in a second position to stimulate a second portion of cardiac tissue, wherein the second stimulation electrode is positioned through a sternotomy;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

31. A method of performing a medical procedure, comprising:
positioning a first stimulation electrode in a first position to stimulate a first portion of cardiac tissue;
positioning a second stimulation electrode in a second position to stimulate a second portion of cardiac tissue, wherein the second stimulation electrode is positioned through a percutaneous incision;
positioning a third stimulation electrode in a third position to stimulate a nerve; providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

32. The method of claim 31 wherein the second portion of cardiac tissue is at least a portion of a heart chamber.

33. The method of claim 32 wherein the heart chamber is a ventricle.

34. The method of claim 32 wherein the heart chamber is an atrium.

35. The method of claim 31 wherein the percutaneous incision is made in a torso of a patient.

36. The method of claim 31 wherein the percutaneous incision is made in a leg of a patient.

37. The method of claim 31 wherein the percutaneous incision is made in an arm of a patient.

38. The method of claim 31 wherein the percutaneous incision is made in a neck of a patient.

39. The method of claim 31 wherein the second position is an endocardial position.

40. A method of performing a medical procedure, comprising:
positioning a first stimulation electrode in a first position to stimulate a first portion of cardiac tissue;
positioning a second stimulation electrode in a second position to stimulate a second portion of cardiac tissue, wherein the second position is an epicardial position;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

41. A method of performing a medical procedure, comprising:
positioning a first stimulation electrode in a first position to stimulate a first portion of cardiac tissue;
positioning a second stimulation electrode in a second position to stimulate a second portion of cardiac tissue, wherein the second position is a myocardial position;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

42. A method of performing a medical procedure, comprising:
positioning a first stimulation electrode in a first position to stimulate a first portion of cardiac tissue;
positioning a second stimulation electrode in a second position to stimulate a second portion of cardiac tissue, wherein the second position is a venous position;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

43. A method of performing a medical procedure, comprising:
positioning a first stimulation electrode in a first position to stimulate a first portion of cardiac tissue;
positioning a second stimulation electrode in a second position to stimulate a second portion of cardiac tissue, wherein the second position is an arterial position;
positioning a third stimulation electrode in a third position to stimulate a nerve;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

44. A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third stimulation electrode is positioned through a thoracotomy;
providing stimulation energy to the first stimulation electrode to stimulate the first portion of cardiac tissue to contract;

providing stimulation energy to the second stimulation electrode to stimulate the second portion of cardiac tissue to contract in synchrony with the first portion of cardiac tissue; and providing stimulation energy to the third stimulation electrode to stimulate the nerve.

45. A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third stimulation electrode is positioned through a sternotomy;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

46. A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third stimulation electrode is positioned through a percutaneous incision;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

47. The method of claim 46 wherein the percutaneous incision is made in a torso of a patient.

48. The method of claim 46 wherein the percutaneous incision is made in a leg of a patient.

49. The method of claim 46 wherein the percutaneous incision is made in an arm of a patient.

50. The method of claim 46 wherein the percutaneous incision is made in a neck of a patient.

51. A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third position is a venous position;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

52. 1he A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third position is an arterial position;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

53. A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third position is an esophageal position;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

54. The A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third position is a tracheal position;
providing stimulation energy to the first stimulation electrode to stimulate the first portion of cardiac tissue to contract;
providing stimulation energy to the second stimulation electrode to stimulate the second portion of cardiac tissue to contract in synchrony with the first portion of cardiac tissue; and
providing stimulation energy to the third stimulation electrode to stimulate the nerve.

55. A method of performing a medical procedure, comprising:
positioning a first stimulation electrode in a first position to stimulate a first portion of cardiac tissue;
positioning a second stimulation electrode in a second position to stimulate a second portion of cardiac tissue;
positioning a third stimulation electrode in a third position to stimulate a nerve, wherein the third position is a cutaneous position;

providing stimulation energy to the first stimulation electrode to stimulate the first portion of cardiac tissue to contract;

providing stimulation energy to the second stimulation electrode to stimulate the second portion of cardiac tissue to contract in synchrony with the first portion of cardiac tissue; and providing stimulation energy to the third stimulation electrode to stimulate the nerve.

56. A method of performing a medical procedure, comprising:

positioning a first stimulation electrode in a first position to stimulate a first portion of cardiac tissue;

positioning a second stimulation electrode in a second position to stimulate a second portion of cardiac tissue;

positioning a third stimulation electrode in a third position to stimulate a nerve;

providing stimulation energy to the first stimulation electrode to stimulate the first portion of cardiac tissue to contract;

providing stimulation energy to the second stimulation electrode to stimulate the second portion of cardiac tissue to contract in synchrony with the first portion of cardiac tissue, wherein a cardiac stimulator provides the stimulation energy to the first and second stimulation electrodes and wherein the cardiac stimulator is an external cardiac stimulator; and providing stimulation energy to the third stimulation electrode to stimulate the nerve.

57. A method of performing a medical procedure, comprising:

positioning a first stimulation electrode in a first position to stimulate a first portion of cardiac tissue;

positioning a second stimulation electrode in a second position to stimulate a second portion of cardiac tissue;

positioning a third stimulation electrode in a third position to stimulate a nerve;

providing stimulation energy to the first stimulation electrode to stimulate the first portion of cardiac tissue to contract;

providing stimulation energy to the second stimulation electrode to stimulate the second portion of cardiac tissue to contract in synchrony with the first portion of cardiac tissue; and providing stimulation energy to the third stimulation electrode to stimulate the nerve, wherein a nerve stimulator provides the stimulation energy to the third stimulation electrode and wherein the nerve stimulator is an external nerve stimulator.

58. A method of performing a medical procedure, comprising:

positioning a first stimulation electrode in a first position to stimulate a first portion of cardiac tissue;

positioning a second stimulation electrode in a second position to stimulate a second portion of cardiac tissue;

positioning a third stimulation electrode in a third position to stimulate a nerve;

providing stimulation energy to the first stimulation electrode to stimulate the first portion of cardiac tissue to contract;

providing stimulation energy to the second stimulation electrode to stimulate the second portion of cardiac tissue to contract in synchrony with the first portion of cardiac tissue;

providing stimulation energy to the third stimulation electrode to stimulate the nerve; and a sensor to detect an inflammatory agent.

59. The method of claim 58 wherein a nerve stimulator in communication with the sensor provides the stimulation energy to the third stimulation electrode.

60. A method of performing a medical procedure, comprising:

providing stimulation energy from a cardiac stimulator to a first stimulation electrode to stimulate a first portion of cardiac tissue;

providing stimulation energy from the cardiac stimulator to a second stimulation electrode to simultaneously stimulate a second portion of cardiac tissue; and providing stimulation energy from a nerve stimulator to a third stimulation electrode to stimulate a vagal nerve.

61. The method of claim 60 further comprising stimulating the vagal nerve while stimulating the first and second portions of cardiac tissue.

62. The method of claim 60 further comprising stimulating the vagal nerve while stopping simultaneous stimulation of the first and second portions of cardiac tissue.

63. The method of claim 60 further comprising stimulating the first and second portions of cardiac tissue while stopping stimulation of the vagal nerve.

64. The method of claim 60 further comprising delivering at least one drug during the medical procedure.

65. The method of claim 60 wherein a cardiac stimulator provides the stimulation energy to the first and second stimulation electrodes.

66. The method of claim 65 wherein the cardiac stimulator is an external cardiac stimulator.

67. The method of claim 65 wherein the cardiac stimulator is an implantable cardiac stimulator.

68. The method of claim 60 wherein a nerve stimulator provides the stimulation energy to the third stimulation electrode.

69. The method of claim 68 wherein the nerve stimulator is an external nerve stimulator.

70. The method of claim 68 wherein the nerve stimulator is an implantable nerve stimulator.

71. The method of claim 60 further comprising a sensor.

72. The method of claim 71 wherein a nerve stimulator in communication with the sensor provides the stimulation energy to the third stimulation electrode.

73. The method of claim 71 wherein a cardiac stimulator in communication with the sensor provides the stimulation energy to the first and second stimulation electrodes.

74. A system for performing a medical procedure, comprising:

an implantable nerve stimulator for delivering stimulation energy to one or more nerve stimulation electrodes;

an implantable cardiac stimulator in communication with the nerve stimulator for delivering stimulation energy to two or more stimulation electrodes; and one or more sensors in communication with the nerve stimulator.

75. The system of claim 74 wherein the one or more nerve stimulation electrodes are selected from the group consisting of:

nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes and probe electrodes.

76. The system of claim 74 wherein the two or more cardiac stimulation electrodes are selected from the group consisting of:

cardiac stimulation electrodes, clip electrodes, needle electrodes, probe electrodes, pacing electrodes, epicardial electrodes, patch electrodes, intravascular electrodes, balloon-type electrodes, basket-type electrodes, tape-type electrodes, umbrella-type electrodes, suction-type electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes.

77. The system of claim 74 further comprising one or more sensors in communication with the cardiac stimulator.

78. A system for performing a medical procedure, comprising:

an implantable nerve stimulator for delivering stimulation energy to one or more nerve stimulation electrodes;

an implantable cardiac stimulator in communication with the nerve stimulator for delivering stimulation energy to two or more stimulation electrodes; and one or more sensors in communication with the nerve stimulator and the cardiac stimulator.

79. A device for performing a medical procedure comprising:

a processor;

one or more nerve stimulation electrodes operatively connected to the processor;

two or more cardiac stimulation electrodes operatively connected to the processor; and one or more physician operated switches operatively connected to the processor to allow a physician to regulate stimulation output from the one or more nerve stimulation electrodes and the two or more cardiac stimulation electrodes.

80. The device of claim 79 wherein stimulation output from the one or more nerve stimulation electrodes occurs in an inverse relationship to stimulation output from the two or more cardiac stimulation electrodes.

81. The device of claim 79 wherein stimulation output from the one or more nerve stimulation electrodes occurs during stimulation output from the two or more cardiac stimulation electrodes.

82. The device of claim 79 wherein the switch is a hand switch.

83. The device of claim 79 wherein the switch is a foot switch.

84. The device of claim 79 wherein the switch is a voice-activated switch.

85. The device of claim 79 wherein the switch is a remote switch.

86. The device of claim 79 further comprising a sensor in communication with the processor.

* * * * *